United States Patent
Lu et al.

(10) Patent No.: US 9,782,357 B2
(45) Date of Patent: Oct. 10, 2017

(54) RNAI MOLECULE DELIVERY PLATFORM BASED ON SINGLE-SIRNA AND SHRNA NANOCAPSULES

(71) Applicant: THE REGENTS OF THE UNIVERSITY OF CALIFORNIA, Oakland, CA (US)

(72) Inventors: Yunfeng Lu, Culver City, CA (US); Irvin S. Y. Chen, Palos Verdes Estate, CA (US); Ming Yan, Encino, CA (US); Min Liang, Encino, CA (US); Masakazu Kamata, Los Angeles, CA (US); Jing Wen, Culver City, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 0 days.

(21) Appl. No.: 14/385,430

(22) PCT Filed: Mar. 15, 2013

(86) PCT No.: PCT/US2013/032615
§ 371 (c)(1),
(2) Date: Sep. 15, 2014

(87) PCT Pub. No.: WO2013/138783
PCT Pub. Date: Sep. 19, 2013

(65) Prior Publication Data
US 2015/0071999 A1    Mar. 12, 2015

Related U.S. Application Data

(60) Provisional application No. 61/612,178, filed on Mar. 16, 2012.

(51) Int. Cl.
| | |
|---|---|
| *A61K 9/51* | (2006.01) |
| *A61K 31/7105* | (2006.01) |
| *A61K 47/14* | (2017.01) |
| *A61K 47/18* | (2017.01) |
| *A61K 47/20* | (2006.01) |
| *A61K 47/22* | (2006.01) |
| *A61K 47/42* | (2017.01) |
| *A61K 47/48* | (2006.01) |
| *C12N 15/87* | (2006.01) |
| *A61K 31/713* | (2006.01) |
| *C12N 15/11* | (2006.01) |
| *A61K 47/69* | (2017.01) |
| *A61K 48/00* | (2006.01) |

(52) U.S. Cl.
CPC .......... *A61K 9/5123* (2013.01); *A61K 9/5138* (2013.01); *A61K 9/5192* (2013.01); *A61K 31/713* (2013.01); *A61K 31/7105* (2013.01); *A61K 47/14* (2013.01); *A61K 47/18* (2013.01); *A61K 47/20* (2013.01); *A61K 47/22* (2013.01); *A61K 47/42* (2013.01); *A61K 47/6925* (2017.08); *A61K 47/6933* (2017.08); *C12N 15/111* (2013.01); *C12N 15/87* (2013.01); *A61K 48/00* (2013.01); *C12N 2310/14* (2013.01); *C12N 2320/32* (2013.01)

(58) Field of Classification Search
None
See application file for complete search history.

(56) References Cited

FOREIGN PATENT DOCUMENTS

JP    2010163364 A    7/2010

OTHER PUBLICATIONS

Wen, et al. (2011) "Controlled protein delivery based on enzyme-responsive nanocapsules", Advanced Materials, 23: 4549-53.*
Wang, et al. (2010) Delivery of siRNA therapeutics: barriers and carriers, The American Association of Pharmaceutical Scientists Journal, 12(4): 492-503.*
Rothdiener, et al. (2010) "Targeted delivery of siRNA to CD33-positive tumor cells with liposomal carrier systems", Journal of Controlled Release, 144: 251-58.*
Zhou, et al. (2010) "Aptamer-targeted cell-specific RNA interference", Silence, 1(4): 1-10.*
http://www.sigmaaldrich.com/catalog/product/aldrich/731099?lang=en&region=US, author unknown, published by Sigma-Aldrich, St. Louis, MO, no journal, no vol., no issue, 2 pages long, printed Apr. 29, 2016.*
Koldehoff (2009) "Therapeutic targeting of gene expression by siRNAs directed against BCR-ABL transcripts in a patient with imatinib-resistant chronic myeloid leukemia", Methods in Molecular Biology, 487: 451-66.*
Whitehead, et al. (2009) "Knocking down barriers: advances in siRNA delivery", Nature Reviews: Drug Discovery, 8: 129-138.*
Birmingham et al., "A protocol for designing siRNAs with high functionality and specificity," Nature Protocols, 2(9):2068-78 (2007).
Castanotto and Ross, "The promises and pitfalls of RNA-interference-based therapeutics," Nature, 457(7228):426-433 (2009).
Cheng and Mahato, "siRNA Delivery and Targeting," Molecular Pharmaceutics, 6(3):649-650 (2009).
Crombez et al., "A New Potent Secondary Amphipathic Cell-penetrating Peptide for siRNA Delivery Into Mammalian Cells," Molecular Therapy, 17(1), 95-103 (2009).
Davis et al., "Evidence of RNAi in humans from systemically administered siRNA via targeted nanoparticles," Nature, 464(7291):1067-U140 (2010).

(Continued)

*Primary Examiner* — Robert M Kelly
(74) *Attorney, Agent, or Firm* — Morgan, Lewis & Bockius LLP; Jeffry S. Mann

(57) ABSTRACT

Novel siRNA and shRNA nanocapsules and delivery methods are disclosed herein. These siRNA and shRNA nanocapsules and delivery methods are highly robust and effective. This invention provides a platform for RNAi delivery with low toxicity and long intracellular half-life for practical therapeutic applications.

18 Claims, 22 Drawing Sheets

(56) References Cited

OTHER PUBLICATIONS

Lewis and Wolff, "Systemic siRNA delivery via hydrodynamic intravascular injection," Advanced Drug Delivery Reviews, 59(2-3):115-123 (2007).
Tseng et al., "Lipid-based systemic delivery of siRNA, Advanced Drug Delivery Reviews," 61(9):721-731 (2009).
Singha et al., "Polymers in Small-Interfering RNA Delivery," Nucleic Acid Therapeutics, 21(3) 133-147 (2011).
Wang et al., "Delivery of siRNA Therapeutics: Barriers and Carriers," The AAP Journal, 12(4) 492-503 (2010).
Wen et al., "Controlled Protein Delivery Based on Enzyme-Responsive Nanocapsules," Adv. Mater. 23, pp. 4549-4553 (2011).
Yan et al., "A novel intracellular protein delivery platform based on single-protein nanocapsules," Nature Nanotechnology, 5, pp. 48-53 (2010).
Yuan et al., "Recent advances of siRNA delivery by nanoparticles," Expert Opin., Drug Deliv. 8(4) 521-536 (2011).

\* cited by examiner

FIGURE 8

FIGURE 9
FIG. 9A
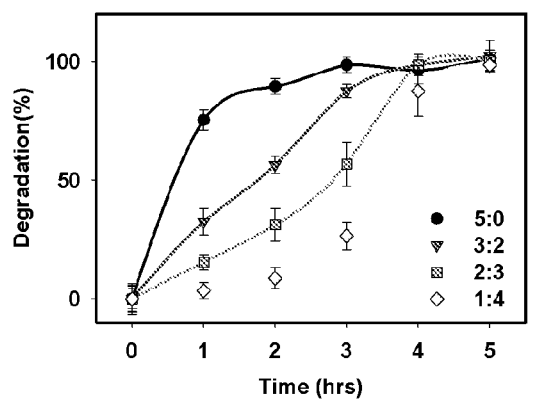
FIG. 9B
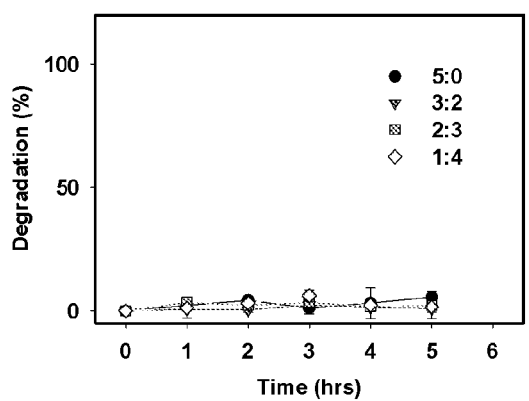

RNAI MOLECULE DELIVERY PLATFORM BASED ON SINGLE-SIRNA AND SHRNA NANOCAPSULES

CROSS-REFERENCE TO RELATED APPLICATIONS

This application claims the benefit under 35 U.S.C. §119(e) to U.S. Application No. 61/612,178 filed Mar. 16, 2012, the disclosure of which is incorporated by reference in its entirety.

GOVERNMENT RIGHTS

This invention was made with Government support under Grant Number HDTRA1-09-1-0001, awarded by the Dept of Defense/Defense Threat Reduction Agency and under Grant Number AI069350, awarded by the National Institutes of Health. The Government has certain rights in the invention.

FIELD OF THE INVENTION

This invention relates to the effective delivery of RNA and DNA molecules into cells by use of novel nanocapsules. Specifically, this invention relates to a novel DNA cassette and siRNA nanocapsule technology wherein DNA molecules or siRNA are encapsulated within a small polymer nanocapsule to facilitate delivery to cells.

BACKGROUND

RNA interference is a powerful tool to target and silence specific gene expression. The term "RNA interference" (RNAi) was coined after the discovery that injection of double stranded RNA (dsRNA) into *C. elegans* leads to specific silencing of genes that are highly homologous in sequence to the delivered dsRNA (Fire et al., 1998). RNAi is closely linked to the post-transcriptional gene-silencing (PTGS) mechanism of co-suppression in plants and quelling in fungi (Catalanotto et al., 2000; Cogoni and Macino, 1999; Dalmay et al., 2000, Ketting and Plasterk, 2000; Mourrain et al., 2000; Smardon et al., 2000).

RNAi was discovered when researchers were attempting to use antisense RNA to inactivate a *C. elegans* gene. The researchers found that injected sense-strand RNA was equally as effective as antisense RNA at inhibiting gene function (Guo et al. (1995) Cell 81: 611-620). Further investigation revealed that the active agent was modest amounts of double-stranded RNA (dsRNA) that contaminated in vitro RNA preparations. Researchers further determined that exon sequences are required and that introns and promoter sequences, while ineffective, did not appear to compromise RNAi.

RNAi can act systemically. This systemic potency was demonstrated by Timmons and Fire (1998 Nature 395: 854). Timmons and Fire performed a simple experiment that produced an astonishing result. They fed to nematodes bacteria that had been engineered to express double-stranded RNA corresponding to the *C. elegans* unc-22 gene. The transgenic nematodes developed a phenotype similar to that of unc-22 mutants. The results of this and variety of other experiments, in *C. elegans* and other organisms, indicate that RNAi acts to destabilize cellular RNA after RNA processing.

Double-stranded RNAs (dsRNAs) can provoke gene silencing in numerous in vivo contexts including *Drosophila, C. elegans*, planaria, hydra, trypanosomes, fungi and plants. Furthermore, short interfering RNA (siRNA), possessing the unique capability to specifically knock down an undesired expression of gene, holds great promises for therapeutics of diversified human diseases. In fact, in it was reported in 2009 that there were 12 ongoing clinical trials using siRNA to treat diseases. Cheng et al., *siRNA Delivery and Targeting*, Molecular Pharmaceutics, 2009, 6(3):649-650. Of the 12 ongoing trials, 8 trials used naked siRNA for local treatment of ocular and respiratory diseases. Castanotto, et al., *The promises and pitfalls of RNA-interference-based therapeutics*, Nature, 2009, 457(7228):426-433. In February 2013, there were 28 siRNA clinical trials reported by the National Institute of Health. See National Institute of Health Clinical Trials website. Many of the 28 trials appear to use naked siRNA.

The clinical application of siRNA is constrained by inefficient delivery systems. Specifically, there is a lack of delivery vehicles that are safe, stable, and efficient. To date, various delivery systems have been proposed. Such systems include cationic liposomes, cell-penetrating peptides (CPPs) and cationic polymers. Tseng et al., *Lipid-based systemic delivery of siRNA*, Advanced Drug Delivery Reviews, 2009, 61(9):721-731 and Lewis et al., *Systemic siRNA delivery via hydrodynamic intravascular injection*, Advanced Drug Delivery Reviews, 2007, 59(2-3):115-123.

Cationic liposomes and cationic lipids, such as Lipofectamine® and lipid-like materials, are used widely for in vitro studies with high effectiveness; however, the toxicity and low efficiency still restrain their in vivo applications.

For the CPPs-based approaches, RNAi molecules are assembled with CPPs or CPP bioconjugates into complexed particles with significantly improved delivery efficiency. Crombez et al., *A New Potent Secondary Amphipathic Cell-penetrating Peptide for siRNA Delivery Into Mammalian Cells*, Molecular Therapy, 2009, 17(1):95-103 and Davis et al., *Evidence of RNAi in humans from systemically administered siRNA via targeted nanoparticles*, Nature, 2010, 464(7291):1067-U140. Nevertheless, the formation of such assembled structure was driven by weak noncovalent interactions and these particles were generally unstable, particularly against serum nucleases which leads to degradation and poor targeting of the RNAi.

For the cationic-polymer-based approaches, siRNA are assembled with cationic polymers is mainly through the electrostatic interactions. The unique proton sponge effect of the cationic polymers provides the complexes with improved intracellular delivery efficiency. However, similar to the CPPs-based approach, such assembled systems are unstable and readily dissociate and release their siRNA payload before they reach the cytoplasm of the target cells.

Accordingly, in spite of such intensive efforts, the design and synthesis of an effective delivery vehicle for siRNA remains challenging. Thus, there is an ongoing need to develop novel siRNA-delivery methods that are highly robust and effective. Success of this work will provide a general delivery platform with low toxicity and long intracellular half-life for practical therapeutic applications.

BRIEF SUMMARY OF THE INVENTION

In certain embodiments, this invention comprises a polymer nanocapsule comprising a polymer shell and a RNAi molecule. In certain embodiments, the polymer shell comprises one or more positively charged monomers selected from Table 1, one or more crosslinkers selected from Table 2, and one or more neutral monomers selected from Table 3. In certain embodiments, the RNAi molecule is siRNA or an shRNA DNA cassette.

In certain embodiments, one or more crosslinkers comprise a ratio of degradable crosslinker to non-degradable crosslinker. In certain embodiments, the ratio of degradable crosslinker to non-degradable crosslinker is selected from the ratios comprising 1:0, 3:2, 2:3, or 1:4. In certain embodiments, all of the crosslinkers are degradable crosslinkers. In certain embodiments, all the degradable crosslinkers are glycerol 1,3-diglycerolate diacrylate.

In certain embodiments, the one or more positively charged monomers is acryl-spermine. In certain embodiments, the one or more positively charged monomers is selected from the group comprising N-(3-Aminopropyl) methacrylamide hydrochloride, Dimethylamino ethyl methacrylate, (3-Acrylamidopropyl)trimethylammonium hydrochloride, and (3-Acrylamidopropyl)trimethylammonium hydrochloride. In certain embodiments, the one or more positively charged monomers is selected from the group comprising N-(3-((44(3-aminopropyl)amino)butyl)amino) propyl)methacrylamide, N-(3-((4-aminobutyl)amino)propyl)acrylamide, N-(3-((4-aminobutyl)amino)propyl)methacrylamide, N-(2-((2-aminoethyl)(methyl)amino)ethyl) acrylamide, N-(2-((2-aminoethyl)(methyl)amino)ethyl) methacrylamide, N-(piperazin-1-ylmethyl)acrylamide, N-(piperazin-1-ylmethyl)methacrylamide, N-(2-(bis(2-aminoethyl)amino)ethyl)acrylamide, and N-(2-(bis(2-aminoethyl)amino)ethyl)methacrylamide.

In certain embodiments, the polymer nanocapsules comprises acryl-spermine, tris-acrylamide, and crosslinker selected from Table 2.

In certain embodiments, the one or more positively charged monomers has 3 protonable amines. In certain embodiments, the one or more positively charged monomers has 2 protonable amines. In certain embodiments, the one or more positively charged monomers has 1 protonable amines.

In certain embodiments, the polymer nanocapsules are approximately 20 nm to 250 nm in diameter.

In certain embodiments, the polymer nanocapsules is conjugated to a targeting agent. In certain embodiments, the targeting agent is selected from the group comprising cyclodextrin, adamantine, CD4, CD8, CD45, aHLA, and transferrin. In certain embodiments, the targeting agent delivers the polymer nanocapsules to a specific cell type, wherein the cell type is selected from the group comprising immune cells, blood cells, cardiac cells, lung cells, optic cells, liver cells, kidney cells, brain cells, cells of the central nervous system, cells of the peripheral nervous system, cancer cells, cells infected with viruses, stem cells, skin cells, intestinal cells, and/or auditory cells. In certain embodiments, the cancer cells are cells selected from the group comprising lymphoma cells, solid tumor cells, leukemia cells, bladder cancer cells, breast cancer cells, colon cancer cells, rectal cancer cells, endometrial cancer cells, kidney cancer cells, lung cancer cells, melanoma cells, pancreatic cancer cells, prostate cancer cells, and thyroid cancer cells.

In certain embodiments, the polymer nanocapsule further comprises a pharmaceutically acceptable carrier.

In certain embodiments, this invention comprises a pharmaceutical composition comprising one or more polymer nanocapsule described above.

In certain embodiments, this invention comprises a method of treating a disease characterized by over expression of a gene with a pharmaceutical composition of a nanocapsules described herein, wherein the siRNA or shRNA knocks down or decreases expression of an over expressed gene, thereby treating the disease.

In certain embodiments, this invention comprises a method of making a siRNA polymer nanocapsules. In certain embodiments, the siRNA is dissolved in RNase-free water. In certain embodiments, one or more positively charged monomers selected from Table 1 and one or more crosslinkers selected from Table 2 in deoxygenated and is dissolved in deionized water to create a monomer mixture. In certain embodiments, the dissolved siRNA as described above is combined with the monomer mixture. In certain embodiments, ammonium persulfate and N,N,N',N'-tetramethylethylenediamine is added to the mixture. In certain embodiments, the mixture is incubated in serum-free medium.

More specifically, Step I depicts: starting with a positively charged, polymerizable monomer, acryl-spermine (1), electrostatic interactions enrich 1 around the surface of the negatively charged siRNA. Step II depicts: subsequent room-temperature polymerization in an aqueous solution, which contains the pH-degradable crosslinkers (2) and hydrophilic monomers (3), wraps each siRNA molecule with a thin shell of polymer network. Step III depicts: a crosslinked shell well protects the cored siRNA from hydrolysis; while tuning the ratio of 1 and 3 allows precise control of the surface charge ensuring the effective cellular transduction of the polymer nanocapsules. Step IV depicts: (2) is stable in neutral pH but is rapidly degraded in acidic environment, such as late endosomes with pH~5.4. It is believed that this unique responsive design will provide the polymer nanocapsules with outstanding stability in serum (pH~7.4), while enabling their escape from endosomes upon the degrading of the shell that releases the siRNA to the cytoplasma. Furthermore, this synthetic approach allows for the immobilization of targeting components (e.g., antibody) to the polymer nanocapsules surface, allowing targeted delivery of siRNA.

Figure 2:
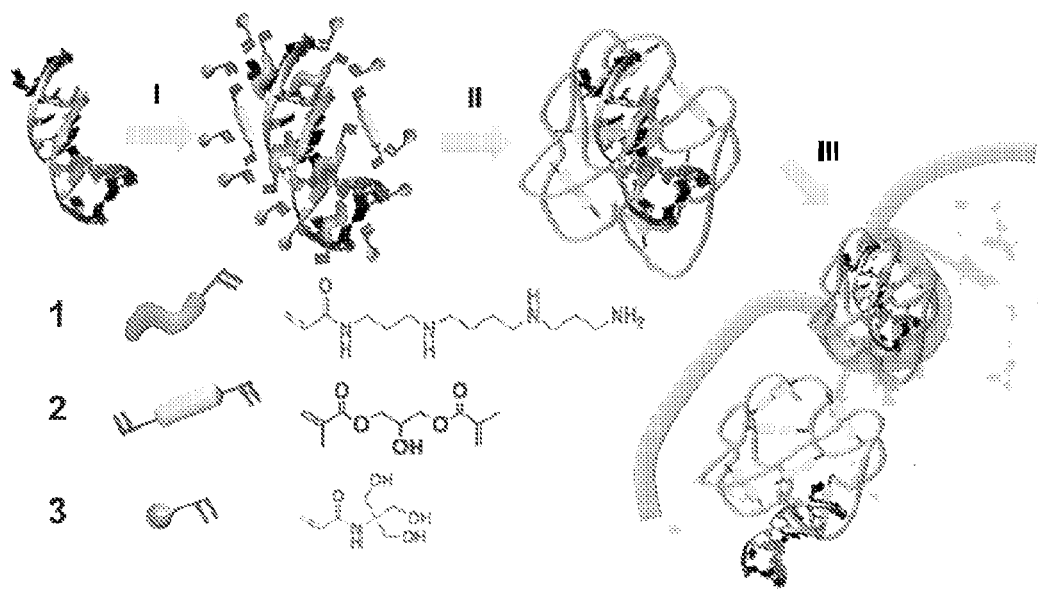
FIG. 2 depicts a schematic illustration of the synthesis and delivery of single siRNA nanocapsules. Step I of the schematic depicts a positively charged, polymerizable monomer that interacts with the negatively charged siRNA. Step II of the schematic depicts the polymerization of pH-degradable crosslinkers and hydrophilic monomers to create a polymer network that that wraps each siRNA molecule. Step III of the schematic depicts crosslinked shell protecting the cored siRNA from hydrolysis. Step IV of the schematic depicts the stability of the polymer nanocapsules in serum (pH~7.4) and their ability to escape from the endosomes upon the degradation of the shell that releases the siRNA to the cytoplasm.
Figure 3:
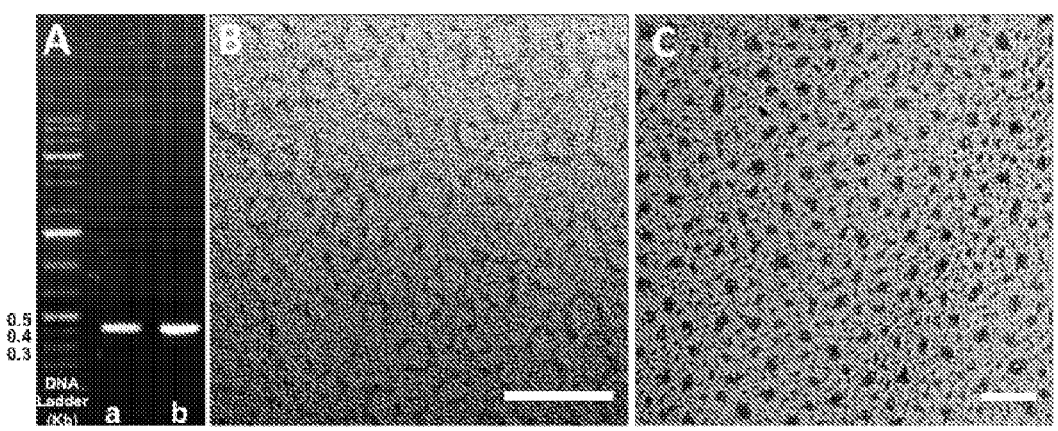

FIG. 3 depicts images and representations of DNA cassettes and nanocapsules. FIG. 2A depicts a gel electrophoresis image of DNA cassette. Lane a is CCR5 shRNA and lane b is EGFP shRNA. FIG. 2B depicts a TEM image of DNA cassettes (Scale bar=100 nm). FIG. 3C depicts a TEM image of DNA cassette nanocapsules (molar ratio of DNA to 3 reactants shown in FIG. 1 and Example 1 and Example 2s A,B,C=1:750:750:30).

Figure 4:
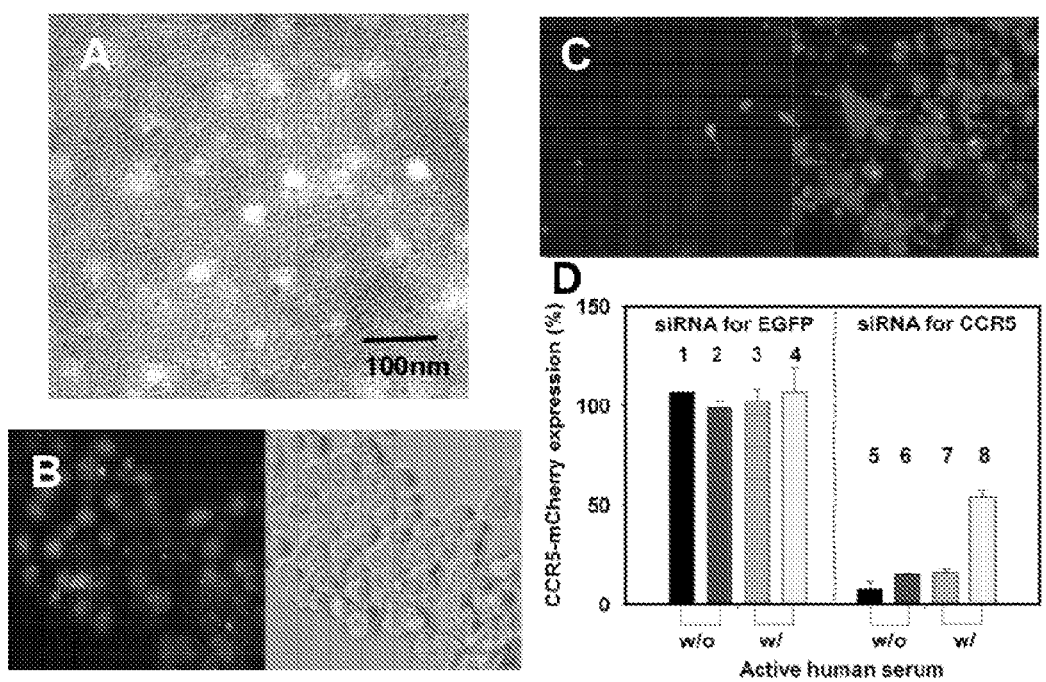

FIG. 4 depicts the polymer nanocapsules and their ability to prevent degradation. FIG. 4A depicts a TEM image of siRNA nanocapsules. FIG. 4B depicts florescence and optical images of HEK-293 T cells transducted with FITC-labeled siRNA nanocapsules. FIG. 4C depicts florescence images of HEK-293 T cells transducted with si1005 siRNA nanocapsules targeted to CCR5 (right) showing knockdown of CCR5-mCherry fusion protein (control siRNA nanocapsules as control (left)). FIG. 4D depicts CCR5-mCherry knock-down by siRNA nanocapsule (1,3,5,7) and siRNA Lipofectamine® (Invitrogen®) (2,4,6,8) in the absence or presence of active human serum.

Figure 5:
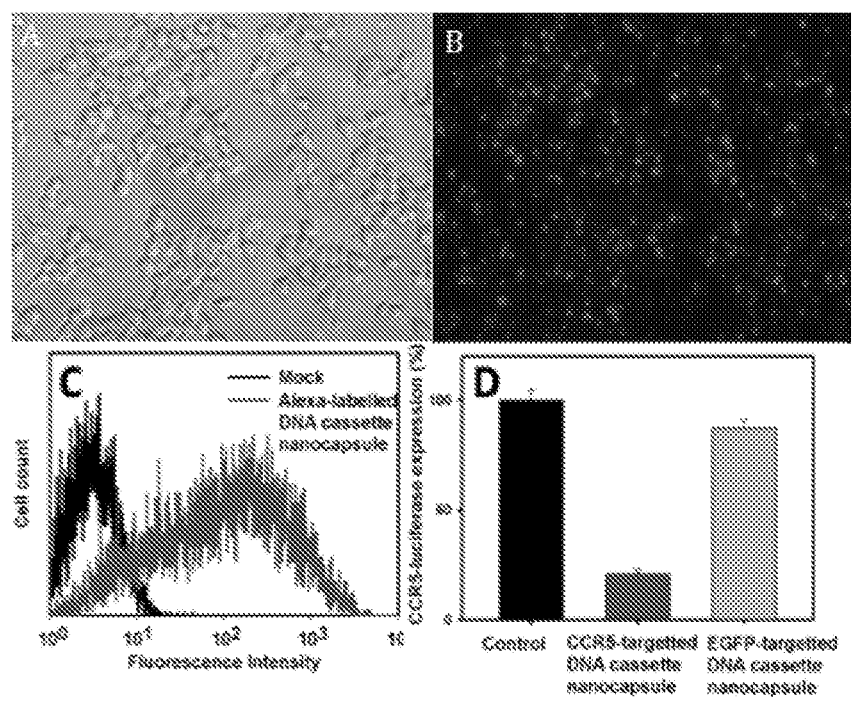

FIG. 5 depicts HEK-293T cells transducted with Alexa592-labelled DNA cassette nanocapsules. FIG. 5A depicts an optical image of the cells. FIG. 5B depicts a fluorescent image of the cells. FIG. 5C depicts a flow cytometry graph of the cells. FIG. 5D depicts the knockdown of CCR5-luciferase by CCR5-shRNA DNA cassette nanocapsules (100 ng DNA per 2.5×104 cells in 100 uL). In these experiments, the cells were dosed with Alexa592-labelled DNA cassette nanocapsules at 100 nM for 4 hours. Then nanocapsules were removed and cells were washed 3 times with PBS. After trypsinization, cells were pictured with Leica Zeiss Axio Observer and also analyzed by a flow cytometer.

Figure 6:
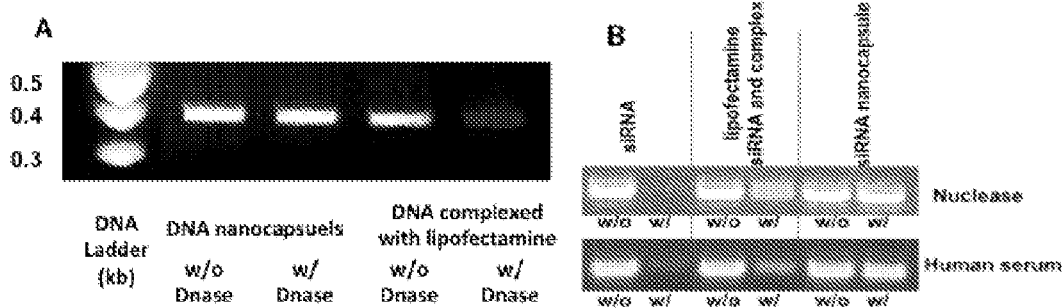

FIG. 6 depicts the sensitivity of DNA cassette to Dnase I and siRNA to nulcease and human serum. FIG. 6A depicts the sensitivity of native DNA cassette and DNA nanocapsules to Dnase I. DNA cassette complexed with Lipofectamine® and DNA nanocapsules were incubated for 1 hour without Dnase I and with Dnase I, respectively. Samples were run on 2% agarose gel and imaged with ImageQuant LAS4000. FIG. 6B depicts the sensitivity of siRNA to Nulcease and serum. siRNA complexed with lipofectamine and siRNA nanocapsules were incubated for 1 hour with nuclease (up) and human serum (down), respectively. Then siRNAs were extracted from lipofectamine and nanocapsules with chloroform/0.1% SDS-0.5 M NaCl. Samples were run on 4% agarose gel and imaged with ImageQuant LAS4000.

Figure 7:
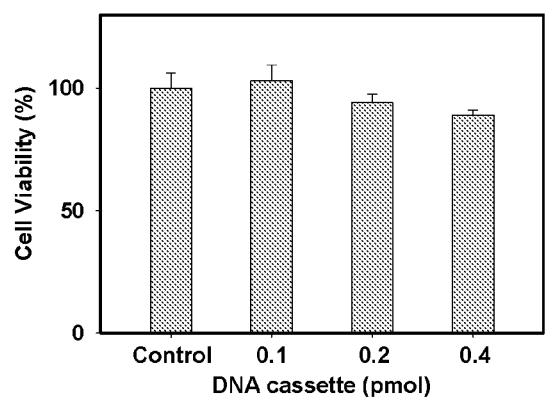

FIG. 7 depicts the viability of HEK-293T cells transducted with CCR5 DNA cassette nanocapsules. HEK-293T cells were treated with DNA cassette nanocapsules at 0, 0.1, 0.2 and 0.4 pmol for 4 h at 37° C. in serum-free medium. Then mediums were changed to DMEM with 10% Bovine Fetal Serum. After 24 h, cell viability was determined through CytoToxGlow kit using a 96-well plate reader.

Figure 8A:
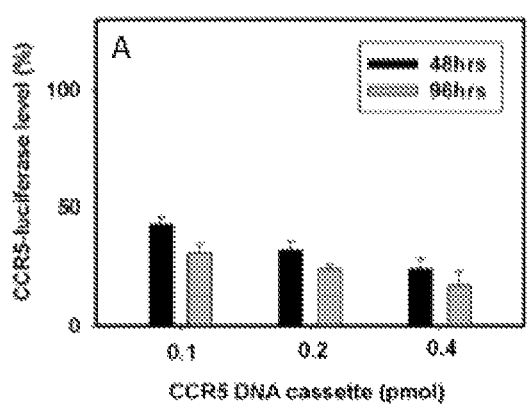
Figure 8B:
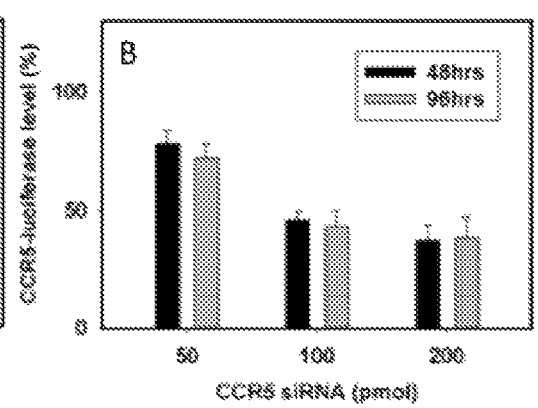

FIG. 8 depicts knockdown of CCR5-Luciferase in HEK-293T cells. FIG. 8A depicts knockdown of CCR5-Luciferase in HEK-293T cells transducted with CCR5 DNA cassette nanocapsules. FIG. 8B depicts knockdown of CCR5-Luciferase in HEK-293T cells transducted with CCR5 siRNA Lipofectamine® complex. HEK-293T cells were treated with DNA cassette nanocapsules at 0, 0.1, 0.2 and 0.4 pmol and siRNA Lipofectamine® complex at 0, 50, 100 and 200 pmol for 4 h at 37° C. in serum-free medium. Then mediums were changed to DMEM with 10% Bovine Fetal Serum. After 48 h, the luciferase activity was determined using a 96-wells plate reader.

FIG. 9 depicts the degradation rates of CCR5-shRNA DNA cassette nanocpsules. FIG. 9A depicts the degradation rates of CCR5-shRNA DNA cassette nanocapsule prepared with cocktails of degradable and non-degradable cross-linkers. FIG. 9B depicts the stability of CCR5-shRNA DNA cassette nanocapsule monitored by DLS in water. The initial shell thickness of the polymer nanocapsules was estimated from $R_0-R^*$, where $R_0$ is the initial diameter of DNA nanocapsules and $R^*$ is the diameter of a DNA molecule (the final diameter after degradation). The degradation degree was calculated as $[R_0-R_t]/[R_0-R^*]\times 100\%$, where $R_t$ is the diameter of nanocapsules.

Figure 10:
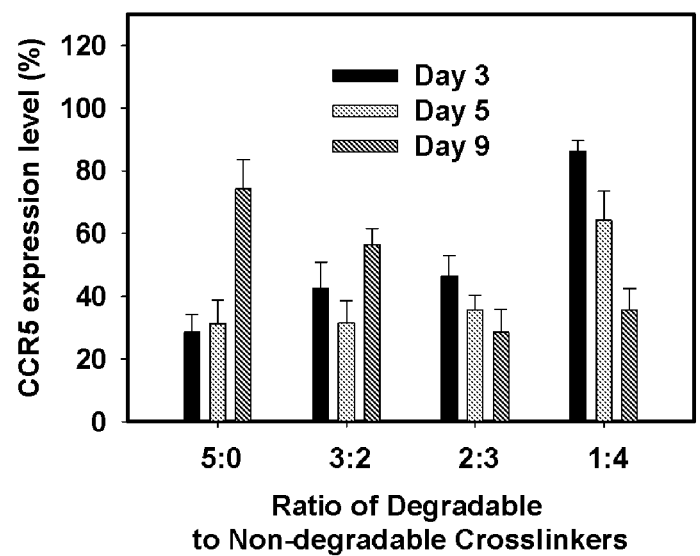

FIG. 10 depicts the down-regulation of CCR5 in HEK293 cells by sh1005 DNA cassette nanocapsules with different ratios (5:0; 3:2; 2:3 and 1:4) of degradable crosslinker (Glycerol 1,3-diglycerolate diacrylate, GDGDA) to non-degradable crosslinker (N,N'-methylenesbisacrylamide, BIS). On day 0 of culture cells were transduced with DNA cassette nanocapsules for 4 hours. On day 3, 5 and 9 of culture cells were labeled with anti-CCR5 and analyzed by flow cytometry.

Figure 11:
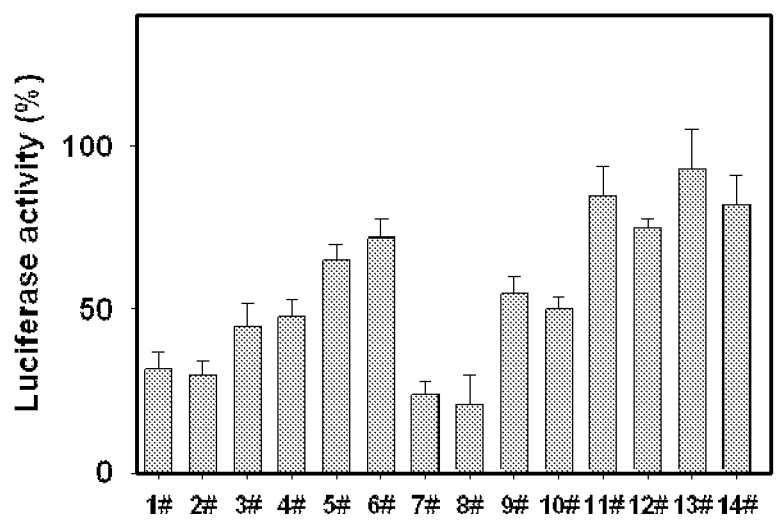

FIG. 11 depicts the ability of nanocapsules prepared with positively charged monomers #1-#14 from Table 1 to knockdown luciferase gene expression in luciferase-expressing CWR cells. As can be seen from the figure, the best knockdown of luciferase expression was achieved with nanocapsules prepared with positively charged monomers #1, #2, #7 and #8.

Figure 12:
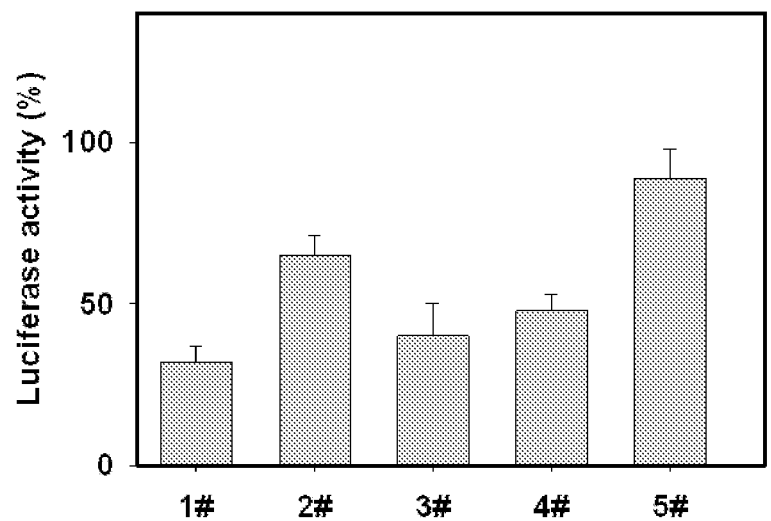

FIG. 12 depicts the ability of nanocapsules prepared with crosslinkers #1-#5 from Table 2 to knockdown luciferase gene expression in luciferase-expressing CWR cells. As can be seen from the figure, the best knockdown of luciferase expression was achieved with nanocapsules prepared with crosslinker #1 (i.e., 2-hydroxyethyl methacrylate).

Figure 13:
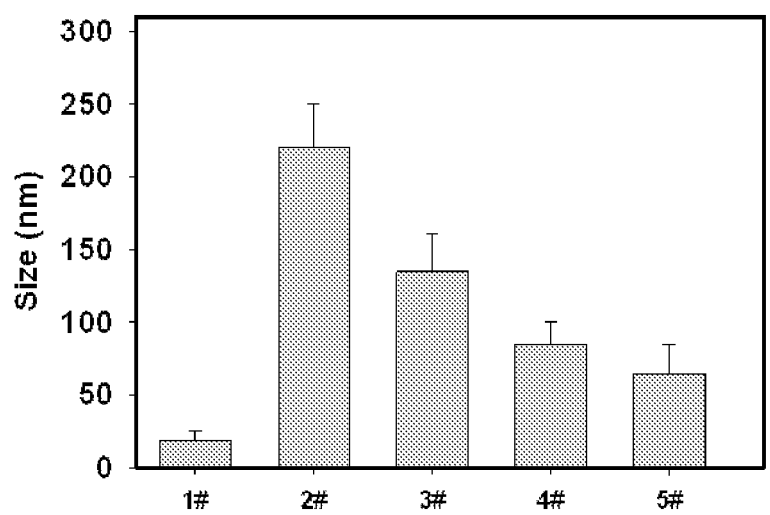

FIG. 13 depicts the ability of neutral monomers to affect the size of the siRNA nanocapsules. As can be seen in the figure, N-(1,3-dihydroxy-2-(hydroxymethyl) propan-2-yl) acrylamide produced the smallest nanocapsules (less than 25 nm) and acrylamide produced the largest nanocapsules (greater than 200 nm).

Figure 14:
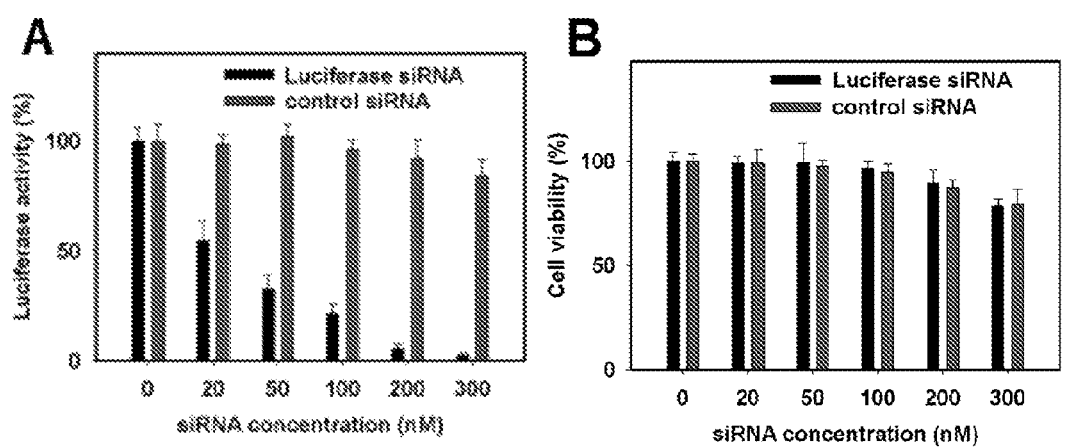

FIG. 14 depicts the knockdown of luciferase gene expression by using luciferase siRNA nanocapsules. FIG. 14A depicts the knockdown of luciferase gene expression in CWR cells using luciferase siRNA nanocapsules and control siRNA nanocapsules. FIG. 14B depicts the cell viability after treatment of siRNA nanocapsules. CWR cells were treated with siRNA nanocapsules at 0, 20, 50, 100, 200 and 300 nM for 4 h at 37° C. in serum-free medium. Then mediums were changed to DMEM with 10% Bovine Fetal Serum. After 48 h, the luciferase activity was determined using a 96-wells plate reader.

Figure 15:
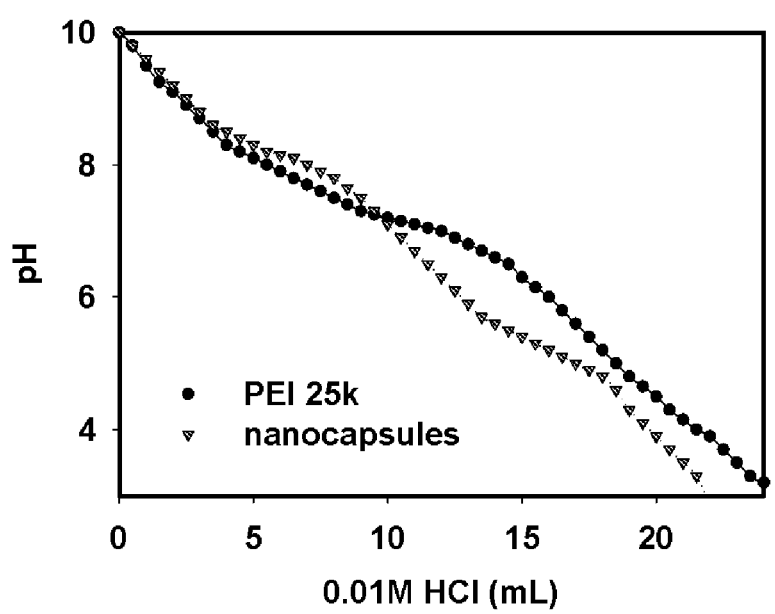

FIG. 15 depicts the pH titration curve of nanocapsules and confirms that one of the polymer nanocapsules has about 60% of buffer capacity of PEI25K between pH 7.3 and 5.5. The buffering capacity of the nanocapsule was measured by acid-base titration. The nanocapsule solutions (8.3 mM in terms of total molar concentration of ioniziable amine groups), which were initially adjusted to pH 10, were titrated with 0.01M HCl. The pH profiles were recorded at room temperature.

Figure 16:
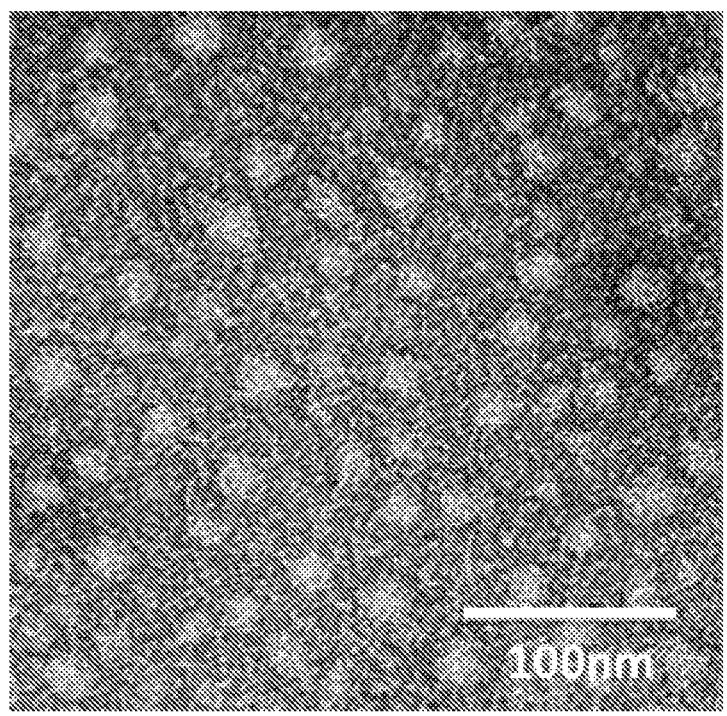

FIG. 16 depicts the TEM picture of BSA control nanoparticle. It is synthesized using the same formulation as that of siRNA nanocapsules and does not show the dark cores in the image. BSA was dissolved in 20 uL Rnase-free water at 20 uM. Then a specific amount of acryl-spermine, tris-acrylamide and glycerol dimethacrylate (molar ratio=5:5:1) dissolved in 0.5 mL deoxygenated and deionized water was mixed with BSA in the microcentrifugetube (final molar ratio of BSA to acryl-spermine=1:220). Radical polymerization from the surface of BSA was initiated by adding 2 uL of 1% ammonium persulfate solution and 1 μL of 5% N,N,N',N'-tetramethylethylenediamine (final molar ratio of BSA to acryl-spermine=1:240). The reaction was allowed to proceed for 60 min in a nitrogen atmosphere.

Figure 17:
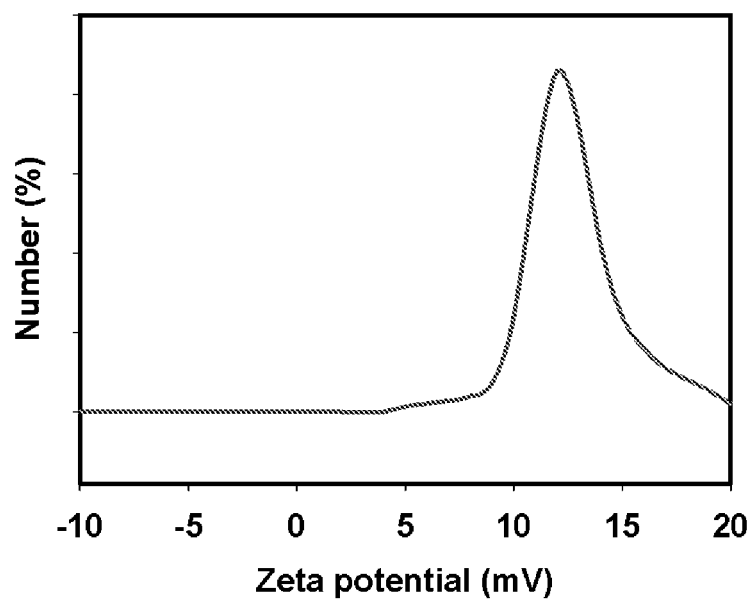

FIG. 17 depicts the surface charge of one of the siRNA nanocapsules determined by dynamic light scattering.

Figure 18:
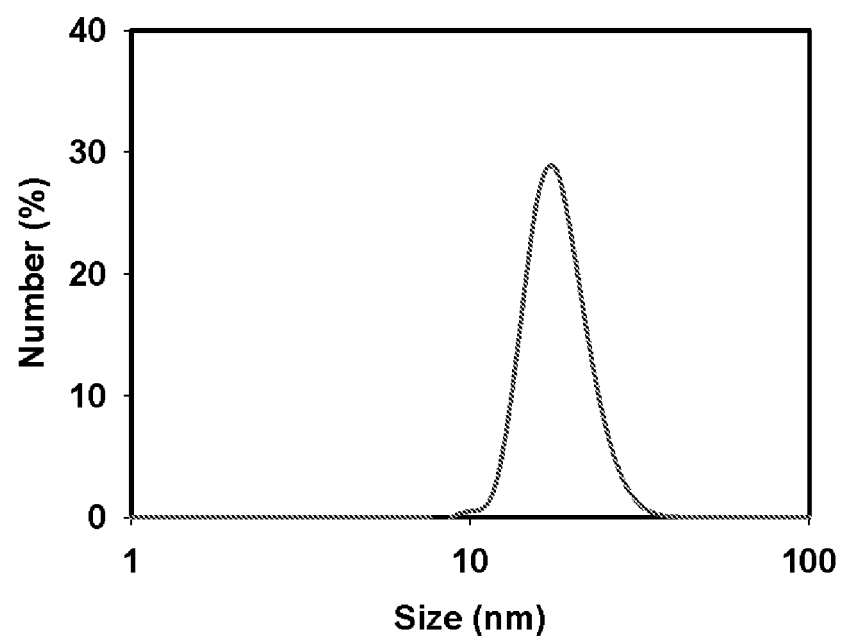

FIG. 18 depicts the size and size distribution of one of the siRNA nanocapsules determined by dynamic light scattering. The average diameter of 24.6 nm obtained by light scattering is consistent with the average diameter of 20 nm obtained by TEM.

Figure 19:
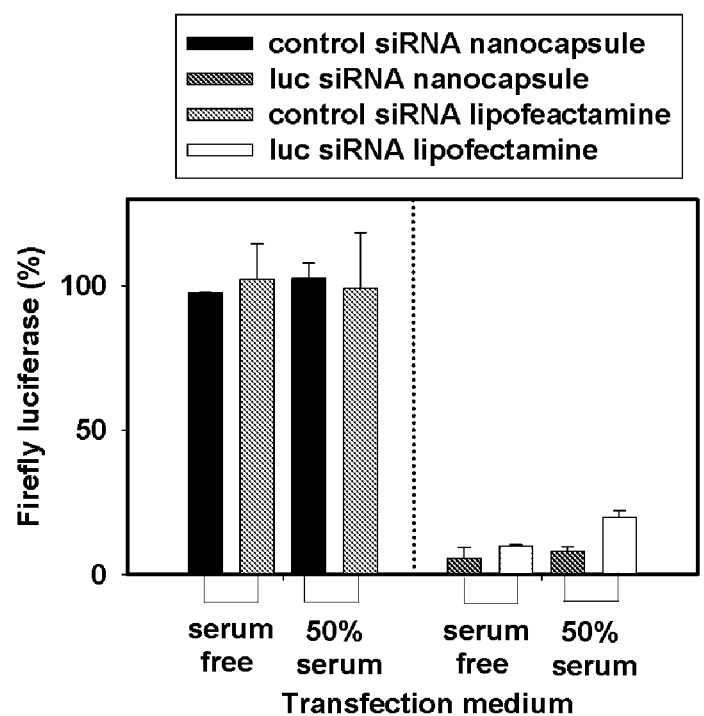

FIG. 19 depicts the knockdown of luciferase by one of the siRNA nanocapsules in the presence and absence of serum.

Figure 20:
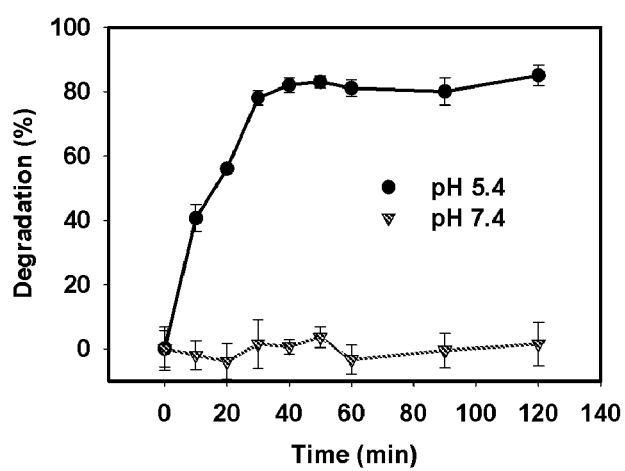

FIG. 20 depicts the degradation profile of siRNA nanocapsules under pH 5.4 or pH 7.4.

Figure 21:
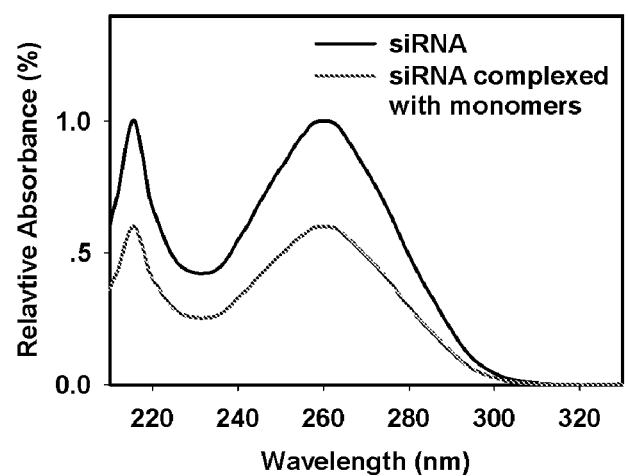

FIG. 21 depicts the absorption change of siRNA after self-assembling with monomers. The absorption of siRNA (top) decreased after formation of siRNA-monomers complex (bottom).

Figure 22:
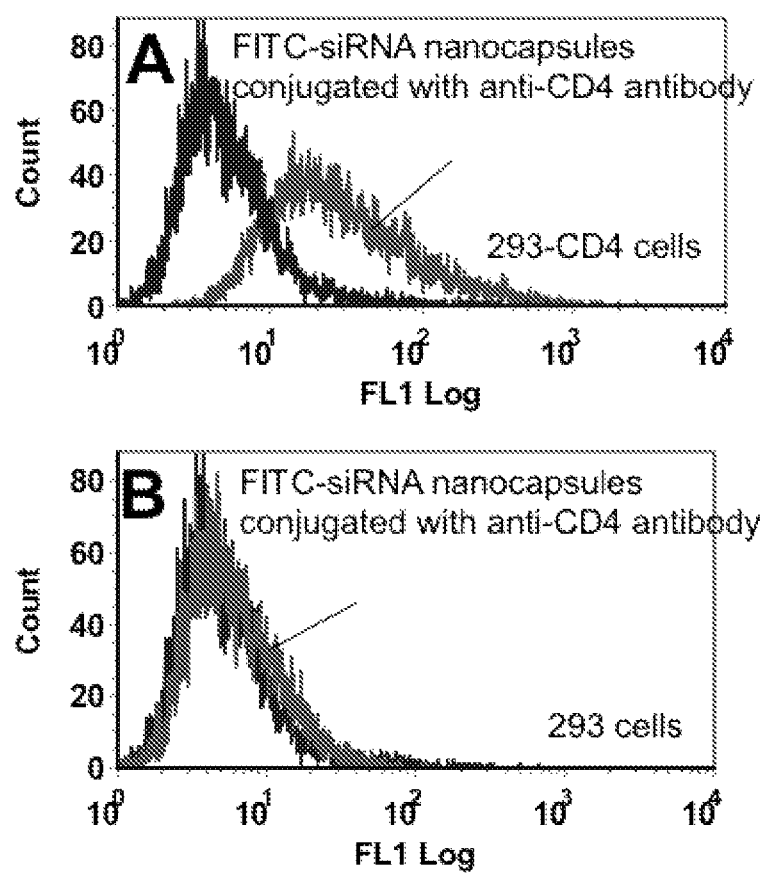

FIG. 22 depicts the targeting delivery of siRNA to 293 cells expressing CD4 receptors.

FIG. 22A shows the flow cytometry graph of 293 cells expressing CD4 receptors after incubation with FITC-labeled siRNA nanocapsules conjugated with anti-CD4 antibody for 4 hours. FIG. 22B shows the flow cytometry graph of regular 293 cells without CD4 receptors after incubation with FITC-labeled siRNA nanocapsules conjugated with anti-CD4 antibody for 4 hours. 100 uL of anti-CD4 antibody dissolved in pH=8.7 HEPES buffer at 1 mg/mL reacted with 10 uL of 2-Iminothiolane (Trout's reagent) at 1 mg/mL for 30 minutes. The modified anti-CD4 antibody will be then incubated with 100 uL of FITC-labeled siRNA nanocapsules at 10 uM overnight.

DEFINITIONS

For convenience, the meaning of certain terms and phrases used in the specification, examples, and appended claims, are provided below.

As used herein, the terms "target" refers to a section of a DNA or RNA strand of a double-stranded DNA or an RNA that is complementary to a section of a DNA or RNA strand, including all transcribed regions, that serves as a matrix for transcription. A target gene, usually the sense strand, is a gene whose expression is to be selectively inhibited or silenced through RNA interference.

As used herein, the term "polymer nanocapsules" refers to a composition comprising a "polymer shell" and a "RNAi molecule."

As used herein, the term "polymer shell" refers to the polymer portion of the RNAi polymer nanocapsules comprising one or more positively charged polymer monomers, one or more crosslinkers, and optionally one or more neutral polymer monomers. Examples of positively charged monomers, crosslinkers, and neutral monomers are provided in Table 1, Table 2, and Table 3.

As used herein, the term "RNAi molecule" refers to a RNA or DNA molecule that plays a role in RNA interference. Specifically, an RNAi molecule refers to a shRNA, siRNA, or dsRNA as disclosed herein. A small hairpin RNA (shRNA) is a RNA sequence that forms a tight hairpin turn that can be used to silence gene expression by RNA interference. shRNAs can be delivered to target cells using DNA plasmids, viral vectors, or bacterial vectors. As used herein, shRNA can be delivered to cells using DNA cassettes. Double-stranded RNAs (dsRNA) comprise a broad group of viruses. Small interfering RNA (siRNA) is a class of double stranded RNA molecules. siRNAs are short, generally around 20-25 base pairs in length. siRNA can be used to silence gene expression by RNA interference. Furthermore, siRNA can also act in RNAi-related pathways such as viral and retroviral infection.

As used herein, the terms "degradable polymer" and "nondegradable polymer" refer to the ability of the polymers described herein to degrade into smaller fragments. In certain embodiments of this invention, degradable polymers can break down at physiological pH. In certain embodiments, degradable polymers can break down at approximately pH 7.4. In certain embodiments, a mixture of degradable and nondegradable polymers can yield a degradable polymer mixture. In certain embodiments, a mixture of degradable and nondegradable polymers can break down at physiological pH. In certain embodiments, a mixture of degradable and nondegradable polymers can break down at approximately pH 7.4.

As used herein, the terms "mutant gene" and "target mutant gene" refer to a gene comprising at least one point mutation relative to the corresponding normal, non-mutated cellular gene (referred to herein as the "corresponding wild-type gene"). The terms mutant gene and target mutant gene specifically encompass any variant of a normal cellular gene or gene fragment whose expression is associated with a disease or disorder (e.g., an oncogene).

As used herein, the term "conjugate" or "conjugate agent" or "surface-conjugated targeting agent" or "polymer nanocapsule conjugates" refers to any moiety, such as a protein or effective portion thereof, that is conjugated to the polymer nanocapsules and provides specific targeting of the polymer nanocapsules to the surface of a specific cell type thereby providing directed delivery of the siRNA or shRNA to a specific cell type. For example, the conjugate agent can binding to a cell-specific cell surface receptor, thereby bringing the polymer nanocapsules into immediate proximity to the target cell. In certain embodiments, the conjugates used to achieve specific targeting of the polymer nanocapsules include CD4, CD8, CD45, CD133, aHLA, and transferrin. In other embodiments, the conjugates can be cell-specific antibodies or fragments thereof. Additional examples of conjugates used to target specific cell types are described below in the Detailed Description.

The term "complementary RNA strand" (also referred to herein as the "antisense strand") refers to the strand of a dsRNA which is complementary to an mRNA transcript that is formed during expression of the target gene, or its processing products. As used herein, the term "complementary nucleotide sequence" refers to the region on the complementary RNA strand that is complementary to a region of an mRNA transcript of the target mutant gene (i.e., "the corresponding nucleotide sequence" of the target gene). "dsRNA" refers to a ribonucleic acid molecule having a duplex structure comprising two complementary and antiparallel nucleic acid strands. Not all nucleotides of a dsRNA must exhibit Watson-Crick base pairs. The maximum number of base pairs is the number of nucleotides in the shortest strand of the dsRNA. The RNA strands may have the same or a different number of nucleotides. The complementary nucleotide region of a complementary RNA strand is less than 25, preferably 19 to 24, more preferably 20 to 24, even more preferably 21 to 23, and most preferably 22 or 23 nucleotides in length. The complementary RNA strand is less than 30, preferably fewer than 25, more preferably 21 to 24, and most preferably 23 nucleotides in length. dsRNAs comprising a complementary or antisense strand of this length (known as "short interfering RNA" or "siRNA") are particularly efficient in inhibiting the expression of the target mutant gene. "Introducing into" means uptake or absorption in the cell, as is understood by those skilled in the art. Absorption or uptake of dsRNA can occur through cellular processes, or by auxiliary agents or devices. For example, for in vivo delivery, dsRNA can be injected into a tissue site or administered systemically. In vitro delivery includes methods known in the art such as electroporation and lipofection.

As used herein, "selective inhibition of expression" means that a dsRNA has a greater inhibitory effect on the expression of a target mutant gene than on the corresponding wild-type gene. Preferably, the expression level of the target mutant gene is less than 98%, less than 95%, less than 90%, less than 80%, less than 70%, less than 60%, less than 50%, less than 40%, less than 30%, less than 20%, or less than 10% of the expression level of the corresponding wild-type gene.

As used herein and as known in the art, the term "identity" is the relationship between two or more polynucleotide sequences, as determined by comparing the sequences. Identity also means the degree of sequence relatedness between polynucleotide sequences, as determined by the match between strings of such sequences. Identity can be readily calculated (see, e.g., Computation Molecular Biology, Lesk, A. M., eds., Oxford University Press, New York (1998), and Biocomputing: Informatics and Genome Projects, Smith, D. W., ed., Academic Press, New York (1993), both of which are incorporated by reference herein). While there exist a number of methods to measure identity between two polynucleotide sequences, the term is well known to skilled artisans (see, e.g., Sequence Analysis in Molecular Biology, von Heinje, G., Academic Press (1987); and Sequence Analysis Primer, Gribskov., M. and Devereux, J., eds., M. Stockton Press, New York (1991)). Methods commonly employed to determine identity between sequences include, for example, those disclosed in Carillo, H., and Lipman, D., SIAM J. Applied Math. (1988) 48:1073. "Substantially identical," as used herein, means there is a very high degree of homology (preferably 100% sequence identity) between the sense strand of the dsRNA and the corresponding part of the target gene. However, dsRNA having greater than 90% or 95% sequence identity may be used in the present invention, and thus sequence variations that might be expected due to genetic mutation, strain polymorphism, or evolutionary divergence can be tolerated. Although 100% identity is preferred, the dsRNA may contain single or multiple base-pair random mismatches between the RNA and the target gene.

As used herein, the term "treatment" refers to the application or administration of a therapeutic agent to a patient, or application or administration of a therapeutic agent to an isolated tissue or cell line from a patient, who has a disorder, e.g., a disease or condition, a symptom of disease, or a predisposition toward a disease, with the purpose to cure, heal, alleviate, relieve, alter, remedy, ameliorate, improve, or affect the disease, the symptoms of disease, or the predisposition toward disease.

As used herein, a "pharmaceutical composition" comprises a pharmacologically effective amount of a dsRNA and a pharmaceutically acceptable carrier. As used herein, "pharmacologically effective amount," "therapeutically effective amount" or simply "effective amount" refers to that amount of an RNA effective to produce the intended pharmacological, therapeutic or preventive result. For example, if a given clinical treatment is considered effective when there is at least a 25% reduction in a measurable parameter associated with a disease or disorder, a therapeutically effective amount of a drug for the treatment of that disease or disorder is the amount necessary to effect at least a 25% reduction in that parameter.

The term "pharmaceutically acceptable carrier" refers to a carrier for administration of a therapeutic agent. Such carriers include, but are not limited to, saline, buffered saline, dextrose, water, glycerol, ethanol, and combinations thereof. The term specifically excludes cell culture medium. For drugs administered orally, pharmaceutically acceptable carriers include, but are not limited to pharmaceutically acceptable excipients such as inert diluents, disintegrating agents, binding agents, lubricating agents, sweetening agents, flavoring agents, coloring agents and preservatives. Suitable inert diluents include sodium and calcium carbonate, sodium and calcium phosphate, and lactose, while corn starch and alginic acid are suitable disintegrating agents. Binding agents may include starch and gelatin, while the lubricating agent, if present, will generally be magnesium stearate, stearic acid or talc. If desired, the tablets may be coated with a material such as glyceryl monostearate or glyceryl distearate, to delay absorption in the gastrointestinal tract.

DETAILED DESCRIPTION OF THE INVENTION

Introduction

RNA interference is a powerful tool to silence specific gene expression and a variety of RNAi-based therapies are being considered for human diseases. However, the major impediment to the effective use of RNAi for applications in humans is its effective delivery into cells. For example, transduction of short hairpin shRNA into hematopoietic stem cells by lentiviral vector has shown to allow endogenous synthesis of siRNA and is able to provide sustainable gene silencing. However, the toxic myeloablative regimens used in the transplant procedure and the limited engraftment of gene-modified cells currently constrains wide application.

A variety of non-viral siRNA delivery systems have been proposed, including cationic liposomes, cell-penetrating peptides (CPPs) and cationic polymers. Cationic lipids, such as Lipofectamine® and lipid-like materials, are widely used for in vitro studies and have shown potential for in vivo gene silencing especially in the liver. As an example of the CPPs-based approach, siRNA can be assembled with CPPs or CPP bioconjugates into complexed particles to generate significantly improved delivery efficiency. Nevertheless, the formation of such structures is driven by weak non-covalent interactions and these particles were generally unstable, particularly, against serum nucleases.

For the cationic-polymer-based approach, siRNA can be assembled with cationic polymers mainly through electrostatic interactions. For example, cationic polymer-based nanoparticles with transferrin as a targeting agent have been shown to deliver siRNA molecules to tumors in humans and reduce the expression of the ribonucleotide reductase subunit RRM2, an anti-cancer target. However, similar to the CPP-based approach, such systems are based upon non-covalent electrostatic self-assembly, which have competition from electrolytes and polyions within the bloodstream. Therefore, in spite of intensive efforts, the design and synthesis of an effective delivery vehicle for siRNA remains a challenge.

Despite the challenges described above, siRNA has become one of the most promising and specific drug candidates with broad potential for the treatment of diverse human diseases attributed to their unique ability to regulate specific genes and control the expression of corresponding proteins. Current commercial products for in vitro siRNA delivery include lipofection and nucleofection. Although these two methods are widly applicable in many cell lines, the delivery efficiency and the toxicity in primary cells remains a formidable challenge.

For in vivo delivery of siRNA, siRNA-mediated gene silencing in mammals through systemic administration was achieved using naked siRNA. However this administration is not compatible with and has many limitations for use in human. Several recent studies have shown improved siRNA delivery in mouse models and nonhuman primates using positively charged peptide or proteins like arginine peptide, CpG oligonucleotide and protamine. Crombez et al., *A New Potent Secondary Amphipathic Cell-penetrating Peptide for siRNA Delivery Into Mammalian Cells*, Molecular Therapy, 2009, 17(1):95-103. Another recent study demonstrates the presence of an RNAi mechanism in humans through systemic administration of siRNA a nanoparticles targeted to melanoma cells. Davis et al., *Evidence of RNAi in humans from systemically administered siRNA via targeted nanoparticles*, Nature, 2010, 464(7291):1067-1070. Nevertheless, highly effective delivery to targeting sites still persists as a major obstacle. In addition, potential adverse immune responses caused by the siRNA remains to be solved.

As described herein, highly stabilized RNAi molecule polymer nanocapsules ("polymer nanocapsules") were fabricated through an in situ polymerization technique, which introduced a protective crosslinked degradable polymer shell covering the surface of the RNAi molecules with designed charges and properties. This crosslinked polymer shell provides protection to the RNAi molecules from RNase degradation, temperature dissociation and serum inactivation. Furthermore, degradability of the polymer network assigns a control-releasing property to RNAi molecules, which results in a less intracellular immune response. By adjusting the charge of the polymer nanocapsules, delivery efficiency of RNAi molecules into human cells was achieved. Furthermore, efficient RNAi molecule delivery into a broad variety of cells including 293T, Hela, CEM, and PBMCs was achieved with highly positive-charged nanocapsules.

Furthermore, surface-conjugated targeting agents on optimized nanocapsules provided successful targeted delivery of RNAi molecules into cells of interest, such as T-cells. The diversified and controllable nontargeting and targeting abilities provided to the RNAi molecule delivery will have important implications for many in vitro tests and clinical applications using RNAi molecules to knock down any desired gene expressions.

Polymer Nanocapsules

This invention provides a novel strategy through self-assembly and in situ polymerization technology to imprint RNAi molecules into crosslinked polymer nanocapsules. In certain embodiments, the polymer nanocapsules are approximately 20-100 nm in diameter. The small diameters of the polymer nanocapsules maximize the protection of the RNAi molecules from external RNase attack and serum neutralization.

In specific embodiments, the polymer nanocapsules are 10 nm-20 nm, 20-25 nm, 25 nm-30 nm, 30 nm-35 nm, 35 nm-40 nm, 40 nm-45 nm, 45 nm-50 nm, 50 nm-55 nm, 55 nm-60 nm, 60 nm-65 nm, 70-75 nm, 75 nm-80 nm, 80 nm-85 nm, 85 nm-90 nm, 90 nm-95 nm, 95 nm-100 nm, or 100 nm-110 nm. In specific embodiments, the polymer nanocapsules are approximately 10 nm, 11 nm, 12 nm, 13 nm, 14 nm, 15 nm, 16 nm, 17 nm, 18 nm, 19 nm, 20 nm, 21 nm, 22 nm, 23 nm, 24 nm, 25 nm, 26 nm, 27 nm, 28 nm, 29 nm, 30 nm, 31 nm, 32 nm, 33 nm, 34 nm, 35 nm, 36 nm, 37 nm, 38 nm, 39 nm, 40 nm, 41 nm, 42 nm, 43 nm, 44 nm, 45 nm, 46 nm, 47 nm, 48 nm, 49 nm, 50 nm, 51 nm, 52 nm, 53 nm, 54 nm, 55 nm, 56 nm, 57 nm, 58 nm, 59 nm, 60 nm, 61 nm, 62 nm, 63 nm, 64 nm, 65 nm, 66 nm, 67 nm, 68 nm, 69 nm, 70 nm, 71 nm, 72 nm, 73 nm, 74 nm, 75 nm, 76 nm, 77 nm, 78 nm, 79 nm, 80 nm, 81 nm, 82 nm, 83 nm, 84 nm, 85 nm, 86 nm, 87 nm, 88 nm, 89 nm, 90 nm, 91 nm, 92 nm, 93 nm, 94 nm, 95 nm, 96 nm, 97 nm, 98 nm, 99 nm, 100 nm, 101 nm, 102 nm, 103 nm, 104 nm, 105 nm, 106 nm, 107 nm, 108 nm, 109 nm, 110 nm, 111 nm, 112 nm, 113 nm, 114 nm, 115 nm, 116 nm, 117 nm, 118 nm, 119 nm, or 120 nm in diameter. In specific embodiments the polymer nanocapsules are 120 nm-130 nm, 130 nm-140 nm, 140 nm-150 nm, 150 nm-160 nm, 160 nm-170 nm, 170 nm-180 nm, 180 nm-190 nm, 190 nm-200 nm, 200 nm-210 nm, 220 nm-230 nm, 230 nm-240 nm, 240 nm-250 nm, or larger than 250 nm in diameter.

In certain embodiments, additional advantages of the polymer nanocapsules disclosed herein include nontargeting and targeting ability, higher efficiency, and lower adverse immune response. For example, the higher efficiency may result from increased uptake and more directed delivery.

Furthermore highly stabilized RNAi molecules inside the protective nanocapsule is able to be fully released once the nanostructured polymer shell is degraded in endosomes and lysosomes. In certain embodiments, a nontargeting polymer encapsulated RNAi molecules can be transduced into primary cells such as PBMCs in vitro with superior efficiency and noncytotoxicity compared to the low efficiency and high toxicity resulting from liposome transduction.

Importantly, by choosing and designing appropriate polymer charge, the method of RNAi molecule delivery to specific purposes (such as targeting by conjugating moieties to the polymer nanocapsules as described herein) can be modulated.

In certain embodiments, the ratio of degradable crosslinker to non-degradable crosslinker is 1:1, 1:2, 2:1, 1:3, 2:3, 3:1, 3:2, 4:1, 1:4, 4:3, 3:4, 5:1, 1:5, 2:5, 5:2, 5:3, 3:5, 4:5, 5:4, 6:1, 1:6, 1:7, 7:1, 2:7, 7:2, 3:7, 7:3, 4:7, 7:4, 5:7, 7:5, 6:7, 7:6, 8:1, 1:8, 3:8, 8:3, 5:8, 8:5, 7:8, 8:7, 9:1, 1:9, 2:9, 9:2, 4:9, 9:4, 5:9, 9:5, 7:9, 9:7, 8:9, 9:8, 10:1, 1:10, 3:10, 10:3, 7:10, 10:7, 9:10, 10:9 or any other ratio that one of skill in the art would know to use.

In certain embodiments, the degradable crosslinkers are one or more of crosslinker 1, 2, 3, 4, or 6 in Table 2. In certain embodiments, the non-degradable crosslinkers are crosslinker 5 in Table 2.

In certain embodiments, the polymer nanocapsules are designed to degrade in 1 hour, or 2 hours, or 3 hours, or 4 hours, or 5 hours, or 6 hours, or 7 hours, or 8 hours, or 9 hours, or 10 hours, or 11 hours, or 12 hours, or 13 hours, or 14 hours, or 15 hours, or 16 hours, or 17 hours, or 18 hours, or 19 hours, or 20 hours, or 21 hours, or 22 hours, or 23 hours, or 1 day, or 2 days, or 3 days, or 4 days or 5 days, or 6 days, or 1 week, or 2 weeks, or 3 weeks, or 1 month or any combination thereof. In certain embodiments, the polymer nanocapsules are designed to degrade at any of the above rates at a physiological pH. In specific embodiments, the polymer nanocapsules are designed to degrade at any of the rates above post-administration to a subject in need thereof.

In specific embodiments, RNAi molecules can be effectively delivered to specific sites in vivo. In certain embodiments, a targeting agent (i.e., a conjugate or conjugate agent) is conjugated to the polymer nanocapsule. In certain embodiments the conjugation prevents the dissociation of the targeting agent from the polymer particle. In specific embodiments, cyclodextrin and adamantane can be used for targeting agent conjugation.

In one embodiment, the invention is practiced using nontargeted and targeted polymer nanocapsules RNAi molecule delivery with high efficiency and low toxicity for in vitro testing and in vivo targeting to specific tissues and organs via intravenous injection.

The enhanced stability of RNAi molecules attributed to the cross-linked polymer also ensures its long-lasting circulation in body before it reaches the targeting sites. Overall, the novel RNAi molecule delivery technology described herein has a notable efficiency, augmented stability, and minimal toxicity both in vitro and predicted in vivo.

Monomers and Cross Linkers

Different monomers and crosslinkers can be used to encapsulate the RNAi molecules by in situ polymerization.

In certain embodiments, the positive monomer have the structure:

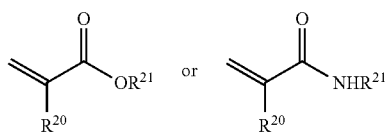

wherein
$R^{20}$ is unsubstituted $C_1$-$C_6$ alkyl
$R^{21}$ is selected from the group consisting of:

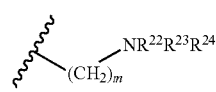

wherein m is an integer from 1 to 5;
$R^{22}$ is H or unsubstituted $C_1$-$C_6$ alkyl or $C_1$-$C_6$ alkyl substituted with $NR^{25}R^{26}$, wherein
  $R^{25}$ and $R^{26}$ are independently selected from H or unsubstituted $C_1$-$C_6$ alkyl or $C_1$-$C_6$ alkyl substituted with amino or $C_1$-$C_6$ alkyl substituted with $NR^{27}R^{28}$, wherein
    $R^{27}$ and $R^{28}$ are independently selected from H or unsubstituted $C_1$-$C_6$ alkyl or $C_1$-$C_6$ alkyl substituted with amino
$R^{23}$ is H or unsubstituted $C_1$-$C_6$ alkyl or $C_1$-$C_6$ alkyl substituted with amino or $C_1$-$C_6$ alkyl substituted with $NR^{29}R^{30}$, wherein
  $R^{29}$ and $R^{30}$ are independently selected from H or unsubstituted $C_1$-$C_6$ alkyl or $C_1$-$C_6$ alkyl substituted with amino or $C_1$-$C_6$ alkyl substituted with $NR^{31}R^{32}$, wherein
    $R^{31}$ and $R^{32}$ are independently selected from H or unsubstituted $C_1$-$C_6$ alkyl or $C_1$-$C_6$ alkyl substituted with amino
and $R^{22}$ and $R^{23}$ are optionally combined to form a 5-7 membered heterocycloalkyl ring; and
$R^{24}$ is a lone pair of electrons or unsubstituted $C_1$-$C_6$ alkyl.

In certain embodiments, the crosslinkers have the structure:

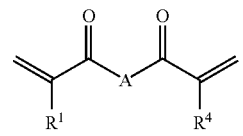

Crosslinkers wherein $R^1$ is unsubstituted $C_1$-$C_6$ alkyl,
$R^4$ is unsubstituted $C_1$-$C_6$ alkyl,
and A is selected from the group consisting of:

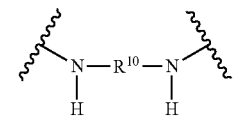

wherein $R^{10}$ is unsubstituted $C_1$-$C_6$ alkylene;
an amino acid;
a peptide consisting of from 2 to 10 amino acids;

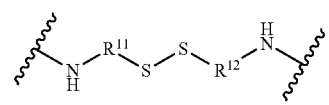

wherein $R^{11}$ is unsubstituted $C_1$-$C_6$ alkylene and $R^{12}$ is unsubstituted $C_1$-$C_6$ alkylene;

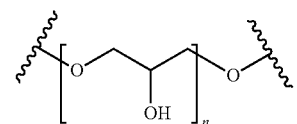

wherein n is from 1 to 10; and

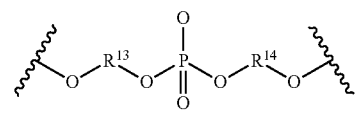

wherein $R^{13}$ is unsubstituted $C_1$-$C_6$ alkylene and $R^{14}$ is unsubstituted $C_1$-$C_6$ alkylene.

In certain embodiments, the neutral monomers have the structure:

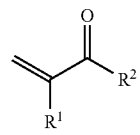

Neutral wherein R1 is unsubstituted C1-C4 alkyl and R2 is amino or amino substituted with hydroxy substituted alkyl or $OR^3$, wherein R3 is hydroxy alkyl.

Non-limiting examples of monomers are presented in Tables 1 and 3. Non-limiting examples of crosslinkers can be found in Table 2. Targeting agents, such as antibodies, peptides, or growth factors can be covalently or noncovalently conjugated with the polymer as described below.

TABLE 1

Non-Limiting Examples of Positively Charged Monomers For RNAi Molecule Polymer Nanocapsules (* monomers are not commercially available and were specifically synthesized for the manufacture of these nanocaspules)

| # | Name | Structure | Number of Protonable amines |
|---|------|-----------|-----------------------------|
| 1 | N-(3-((4-((3-aminopropyl)amino)butyl)amino)propyl)acrylamide* | 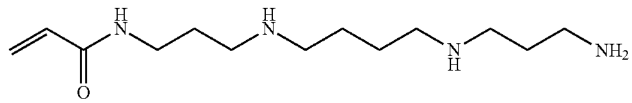 [SMILES: C=CC(=O)NCCCNCCCCNCCCN] | 3 |
| 2 | N-(3-((4-((3-aminopropyl)amino)butyl)amino)propyl)methacrylamide* | 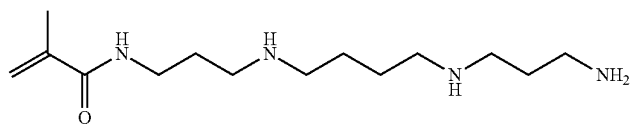 [SMILES: C=C(C)C(=O)NCCCNCCCCNCCCN] | 3 |
| 3 | N-(3-((4-aminobutyl)amino)propyl)acrylamide* | 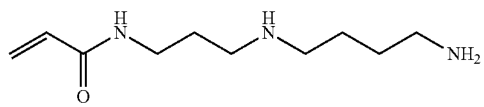 | 2 |
| 4 | N-(3-((4-aminobutyl)amino)propyl)methacrylamide* | 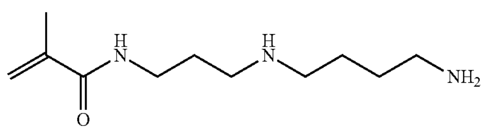 | 2 |
| 5 | N-(2-((2-aminoethyl)(methyl)amino)ethyl)acrylamide* | 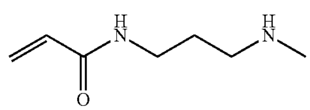 | 1 |
| 6 | N-(2-((2-aminoethyl)(methyl)amino)ethyl)methacrylamide* | 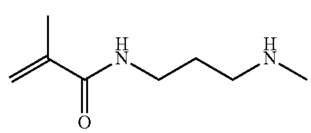 | 1 |
| 7 | N-(piperazin-1-ylmethyl)acrylamide* | 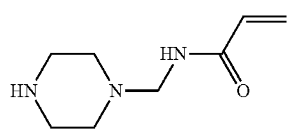 | 2 |
| 8 | N-(piperazin-1-ylmethyl)methacrylamide* | 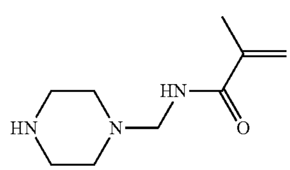 | 2 |
| 9 | N-(2-(bis(2-aminoethyl)amino)ethyl)acrylamide* | 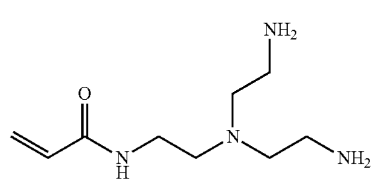 | 3 |
| 10 | N-(2-(bis(2-minoethyl)amino)ethyl)methacrylamide* | 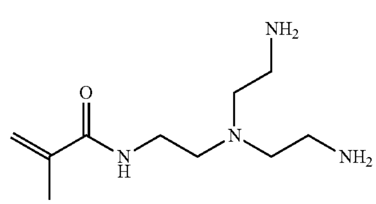 | 3 |

TABLE 1-continued

Non-Limiting Examples of Positively Charged Monomers For RNAi Molecule Polymer Nanocapsules (* monomers are not commercially available and were specifically synthesized for the manufacture of these nanocaspules)

| # | Name | Structure | Number of Protonable amines |
|---|---|---|---|
| 11 | N-(3-Aminopropyl) methacrylamide hydrochloride | 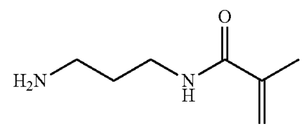 | 1 |
| 12 | Dimethylamino ethyl methacrylate | 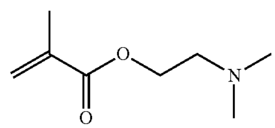 | 1 |
| 13 | (3-Acrylamidopropyl) trimethylammonium hydrochloride | 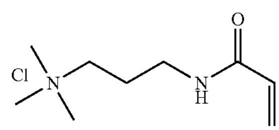 | 1 |
| 14 | 2-aminoethyl methacrylate | 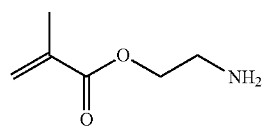 | 1 |

TABLE 2

Non-Limiting Examples of Crosslinkers for RNAi molecule Polymer Nanocapsules.

| # | Name | Structure |
|---|---|---|
| 1 | 1,3-glycerol dimethacrylate | 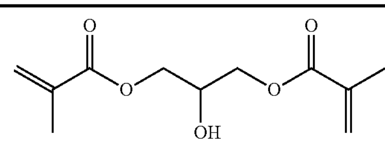 |
| 2 | Glycerol 1,3-diglycerolate diacrylate | 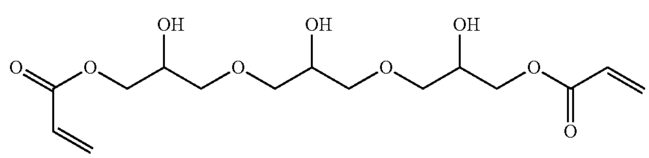 [SMILES: C=CC(=O)OCC(O)COCC(O)COCC(O)COC(=O)C=C] |
| 3 | N,N'-bis(acryloyl)cystamine | 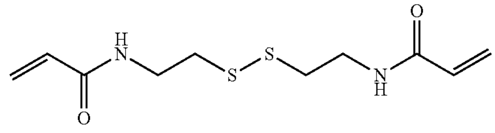 [SMILES: C=CC(=O)NCCSSCCNC(=O)C=C] |
| 4 | bis[2-(methacryloyloxy)ethyl]phosphate | 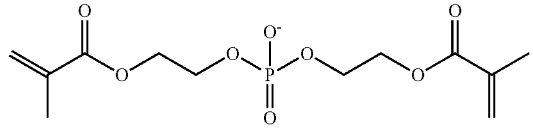 [SMILES: C=C(C)C(=O)OCCOP(=O)([O-])OCCOC(=O)C(=C)C] |
| 5 | N,N'-Methylenebisacrylamide | 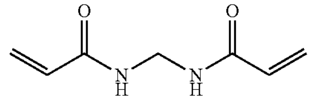 |

TABLE 2-continued

Non-Limiting Examples of Crosslinkers for RNAi molecule Polymer Nanocapsules.

| # Name | Structure |
|---|---|
| 6 bisacryloylated polypeptide | [structure showing bisacryloylated polypeptide] |

TABLE 3

Non-Limiting Examples of Neutral Monomers for RNAi Molecule Polymer Nanocapsules

| # Name | Structure |
|---|---|
| 1 N-(1,3-dihydroxy-2-(hydroxymethyl)propan-2-yl)acrylamide | [structure] |
| 2 acrylamide | [structure] |
| 3 N-(hydroxymethyl)acrylamide | [structure] |
| 4 2-hydroxyethyl acrylate | [structure] |
| 5 2-hydroxyethyl methacrylate | [structure] |

Polymer Nanocapsule Conjugates

In certain embodiments, targeted delivery of RNAi molecules into cells is achieved using surface-conjugated targeting agents on optimized nanocapsules. Of particular interest, the polymer nanocapsule conjugates can be used to target immune, pulmonary, lung, optic, liver, kidney, brain, central nervous system, peripheral nervous system, cardiac, cancer, proliferative, virally or retrovirally infected, stem, skin, intestinal, and/or auditory cells.

In certain embodiments, the conjugates used to achieve specific targeting of the polymer nanocapsules include CD4, CD8, CD45, CD133, aHLA, and transferrin. In certain embodiments, the conjugates used to achieve specific targeting of the polymer nanocapsules include any one or more of the cluster of differentiation or cluster of designation (CD) markers. For example, the CD markers include CDX wherein X can be any one of 1-340. As described herein, the term "CD1", for example, means all CD1 variants and subtypes. This applies to all CD markers described herein.

In certain embodiments, the conjugates used to achieve specific targeting of the polymer nanocapsules include any one or more of AFP, beta-Catenin, BMI-1, BMP-4, c-kit, CXCL12, SDF-1, CXCR4, decorin, E-Cadherin, Cadherin 1, EGFR, ErbB1, Endoglin, EpCAM, TROP-1, Fc epsilon RI A, FCER1A, L1CAM, LMO2, Nodal, Notch-1, PDG-FRB, Podoplanin, PTEN, Sonic Hedgehog, STAT3, Syndecan-1, Tranferrin Receptor, and Vimentin.

In certain embodiments, the conjugates used to achieve specific targeting of the polymer nanocapsules include any one or more of ALK, AFP, B2M, Beta-hCG, BCR-ABL, BRAF, CA15-3, CA19-9, CA-125, Calcitonin, CEA (Carcinoembryonic antigen), CD20, Chromagranin A, Cytokeratin or fragments thereof, EGFR, Estrogen Receptor, Progesterone Receptor, Fibrin, Fibrinogen, HE4, HER2/neu, IgG variants, KIT, lactate dehydrogenase, Nuclear matrix protein 22, PSA, thyroglobulin, uPA, PAI-1, and Oval.

Any marker described herein or known to one of skill in the art can be used alone, or in combination with one or more additional markers, to achieve the desired targeting of specific cells.

All other cell and/or tissue specific markers known to one of skill in the art here incorporated by reference.

Methods of Treating Diseases Caused by Expression of a Target Gene

In one embodiment, the invention relates to a method for treating a subject having a disease or at risk of developing a disease caused by the expression of a target mutant gene.

In certain embodiments, the polymer nanocapsules described herein can act as novel therapeutic agents for controlling one or more of cellular proliferative and/or differentiative disorders. In certain embodiments, the polymer nanocapsules can act as novel therapeutic agents for controlling one or more immune or immunodeficiency disorders. In certain embodiments, the polymer nanocapsules can act as novel therapeutic agents for preventing viral replication or viral infection. In certain embodiments, the polymer nanocapsules can act as novel therapeutic agents for controlling one or more neurological or neurodegenerative disorders. In certain embodiments, the polymer nanocapsules can act as novel therapeutic agents for treating or preventing cancer.

In certain embodiments, the polymer nanocapsules can act as novel therapeutic agents for treating advanced cancers, pachyonychia congenital, age-related macular degeneration, choroidal neovascularization, metastatic melanoma, metastatic melanoma without CNS metastases, chronic myeloid leukemia, solid tumors, advanced solid tumors, optic atrophy, non-arteric anterior ischemic optic neuropathy, pancreatic cancer, pancreatic ductal adenocarcinoma, diavetic macular edema, hypercholesterolemia, colorectal cancer with hepatic metastases, pancreatic cancer with hepatic metastases, gastric cancer with hepatic metastases, breast cancer with hepatic metastases ovarian cancer with hepatic metastases, preeclampsia, neuroblastoma, ocular hypertension, open angle glaucoma, glaucoma, ocular pain, dry eye syndrome, kidney injury, acute renal failure, delayed graft function, complications of kidney transplant, TBX3 overexpression, and diabetic retinopathy.

In specific embodiments, the polymer nanocapsules can act as novel therapeutic agents for treating viral infections. In specific embodiments, the polymer nanocapsules can act as novel therapeutic agents for treating retroviral viral infections. In specific embodiments, the polymer nanocapsules can act as novel therapeutic agents for treating HIV or AIDS infections. In specific embodiments, the polymer nanocapsules can act as novel therapeutic agents for suppressing retroviral viral infections. In specific embodiments, the polymer nanocapsules can act as novel therapeutic agents for blocking, preventing, or downregulating retrovirus or virus replication.

In certain embodiments, the polymer nanocapsules described herein can be administered by intravitreal injection, intravenously, by injection into the callus on the bottom of one foot, by oral administration, subcutaneously, and by any other mode of pharmaceutical administration known to one of skill in the art.

In certain embodiments, the method comprises administering a pharmaceutical composition of the invention to the subject, such that expression of the target mutant gene is silenced or down regulated. In certain embodiments the subject is a mammal. In certain embodiments the mammal is a human. Because of their high specificity, the polymer nanocapsules of the present invention specifically target the mutant genes of diseased cells and tissues, as described herein.

In the prevention of disease, the target gene may be one which is required for initiation or maintenance of the disease, or which has been identified as being associated with a higher risk of contracting the disease. In the treatment of disease, the polymer nanocapsules can be brought into contact with the cells or tissue exhibiting the disease. As one non-limiting example, polymer nanocapsules are substantially identical to all or part of a mutated gene associated with cancer, or one expressed at high levels in tumor cells may be brought into contact with or introduced into a cancerous cell or tumor gene. As another non-limiting example, polymer nanocapsules are substantially identical to all or part of a mutated gene associated with a viral or retroviral disease. Specifically, a non-limiting example of a retroviral disease that can be treated with the polymer nanocapsules described herein is HIV (see FIGS. 3, 4, and 6-10).

Non-limiting examples of cellular proliferative and/or differentiative disorders include cancer, e.g., carcinoma, sarcoma, metastatic disorders or hematopoietic neoplastic disorders, e.g., leukemias. A metastatic tumor can arise from a multitude of primary tumor types, including but not limited to those of prostate, colon, lung, breast and liver origin. As used herein, the terms "cancer," "hyperproliferative," and "neoplastic" refer to cells having the capacity for autonomous growth, i.e., an abnormal state of condition characterized by rapidly proliferating cell growth. These terms are meant to include all types of cancerous growths or oncogenic processes, metastatic tissues or malignantly transformed cells, tissues, or organs, irrespective of histopathologic type or stage of invasiveness. Proliferative disorders also include hematopoietic neoplastic disorders, including diseases involving hyperplastic/neoplatic cells of hematopoietic origin, e.g., arising from myeloid, lymphoid or erythroid lineages, or precursor cells thereof.

Mutations in cellular genes that directly or indirectly control cell growth and differentiation are considered to be the main cause of cancer. There are approximately thirty families of genes, called oncogenes, which are implicated in human tumor formation. Members of one such family, the RAS gene family, are carried in a broad range of eukaryotes and are frequently found to be mutated in human tumors. Polymer nanocapsules of this invention can be used to target such oncogenes to knock down or prevent their expression.

In addition to oncogenes, the methods and compositions of the invention can be applied to other disease-related target genes having a point mutation. Gene mutations have been reported in more than 1000 different human genes. Data on these mutations and their associated phenotypes have been collated and are available online through two major databases: Online Mendelian Inheritance in Man in Baltimore and the Human Gene Mutation Database in Cardiff. For example, there is a high frequency of CG to TG or CA mutations in the human genome due to deamination of 5' methyl-cytosine. Short deletions or insertions of less than 20 nucleotides are also very common mutations in humans. See, e.g., Antonarakis, S. E., Eur. Pediatr. (2000) 159(3): 5173-8.

Furthermore, Sachidanandam et al. describes a map of human genome sequence variation containing 1.42 million single nucleotide polymorphisms, which is useful for identifying biomedically important genes for diagnosis and therapy (Sachidanandam, R., et al., Nature (2001) 409 (6822):821-2 and Nature (2001) 409(6822):822-3). The map integrates all publicly available SNPs with described genes and other genomic features. An estimated 60,000 SNPs fall within exon (coding and untranslated regions), and 85% of exons are within 5 kb of the nearest SNP. Clifford et al. provides expression-based genetic/physical maps of single-nucleotide polymorphisms identified by the cancer genome anatomy project (Clifford, R., et al., Genome Res (2000) 10(8):1259-65). In addition to SNP maps, Sachidanandam et al. provide maps containing SNPs in genes expressed in breast, colon, kidney, liver, lung, or prostate tissue.

Accordingly, RNAi molecule polymer nanocapsules of this invention can be used to target such mutant genes to knock down or prevent their expression Methods of Inhibiting Expression of a Mutant Gene In yet another aspect, the invention relates to a method for inhibiting the expression of a mutant gene in subject. The method comprises administering a composition of the invention to the subject such that expression of the mutant gene is silenced as compared to the corresponding wild-type gene. In certain embodiments the subject is a mammal. In certain embodiments the mammal is a human.

Because of their high specificity, the siRNA nanocapsules of the present invention specifically target RNAs (primary or processed) of target mutant genes, and at surprisingly low dosages. Compositions and methods for inhibiting the expression of a target gene using polymer nanocapsules can be performed as described herein.

In one embodiment, the invention comprises administering a composition comprising polymer nanocapsules, wherein the polymer nanocapsules comprise a nucleotide sequence which is substantially complementary to an RNA transcript of the target mutant gene and partially complementary to the corresponding wild-type gene. When the subject to be treated is a mammal, such as a human, the composition may be administered by any means known in the art including, but not limited to oral or parenteral routes, including intravenous, intramuscular, intraperitoneal, subcutaneous, transdermal, airway (aerosol), rectal, vaginal and topical (including buccal and sublingual) administration. In preferred embodiments, the compositions are administered by intravenous or intraparenteral infusion or injection.

The methods for inhibition the expression of a target gene can be applied to any mutant gene one wishes to silence, thereby selectively inhibiting its expression. Non-limiting examples of human genes which can be targeted for silencing include oncogenes cytokinin gene, idiotype protein genes, prion genes, genes that expresses molecules that induce angiogenesis, genes that encode adhesion molecules, genes that encode cell surface receptors, genes of proteins that are involved in metastasizing and/or invasive processes, genes of proteases as well as of molecules that regulate apoptosis and the cell cycle, genes that express the EGF receptor, genes that encode the multi-drug resistance 1 gene (MDR1 gene), genes that allow viral uptake and replication, genes that cause neurodegenerative disorders, genes that cause protein aggregation and/or accumulation, genes that cause up-regulation or down regulation of hormones, genes that cause neurological disorders, genes that cause cardiac disorders, and genes that cause psychological disorders. One of skill in the art would understand which genes are encompassed by the broad categories of exemplary genes described above.

Methods of Manufacture

In certain embodiments, the polymer nanocapsules described herein are manufactured to achieve a specific size, to target a specific site for gene downregulation, and to downregulate a specific gene. The size of the polymer nanocapsules described herein can be determined based on the polymer:crosslinker ratio as described herein. Targeted delivery can be achieved, for example, using conjugate agents that are attached (i.e., conjugated) to the exterior of the polymer nanocapsules as described herein. Furthermore, the specific binding of an RNAi molecule of a polymer nanocapsules described herein to a specific gene (thereby decreasing specific gene expression) can be achieved by designing the RNAi molecule using methods known to one of skill in the art. See, e.g., Birmingham et al., "A protocol for designing siRNAs with high functionality and specificity," Nature Protocols, 2007; 2(9):2068-78. Furthermore, the ability of the polymer nanocapsules to deliver the RNAi molecules to the target site can be optimized and determined by adjusting the ratios of degradable:nondegradable polymers as described herein.

Methods of Administration

The pharmaceutical compositions encompassed by the invention may be administered by any means known in the art including, but not limited to oral or parenteral routes, including intravenous, intramuscular, intraperitoneal, subcutaneous, transdermal, airway (aerosol), rectal, vaginal and topical (including buccal and sublingual) administration. In preferred embodiments, the pharmaceutical compositions are administered by intravenous or intraparenteral infusion or injection.

EXAMPLES

Example 1. Manufacture of Nanocapsules

Figure 1:
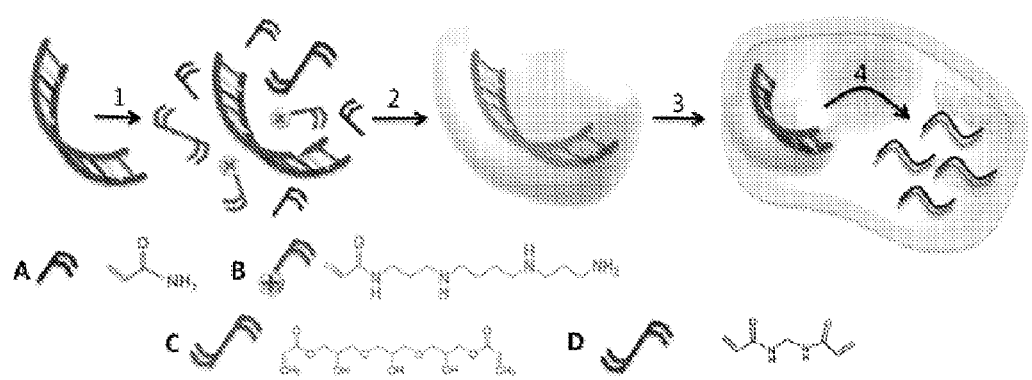
FIG. 1 depicts an illustration of the synthesis and delivery of DNA cassette nanocapsules: 1) self-assembly of hydrophilic monomer A, positively charged monomer B, degradable crosslinker C and non-degradable crosslinker D around DNA cassette; 2): formation of DNA cassette nanocapsules through in situ polymerization; 3): delivery; IV): release of DNA cassette and expression of siRNA.

Highly stabilized siRNA polymer nanocapsules were fabricated through an in situ polymerization technique as described in Example 1 and FIGS. 1 and 2. The manufacture of a siRNA nanocapsule platform depicted in FIG. 1, starts with a positively charged monomer A, a crosslinker B, a neutral co-monomer C and enriches these molecules around the surface of the negatively charged siRNA through electrostatic interaction and hydrogen bonding. A series of positively charged monomers (Table 1), crosslinkers (Table 2) and neutral co-monomers (Table 3) were used in the manufacture of the polymer nanocapsule platform. Different crosslinkers, for example those listed in Table 2, can be used to form copolymer coatings with tunable composition, structure, surface property, and functionality.

This in situ polymerization technique introduced a protective crosslinked degradable polymer shell covering on the surface of the siRNA with designed charges and properties. This crosslinked polymer shell provides protection to the siRNA from RNase degradation, temperature dissociation and serum inactivation. Non-liming examples of crosslinkers that can be used in the siRNA nanocapsules are provided in Table 2.

Example 2. Manufacture of Nanocapsules Using Acryl-Spermine

In this example, the preparation of acryl-spermine was achieved by reacting spermine with acrylic acid, hydroxysuccinimide ester (NAS). Briefly, spermine (100 mg) and NAS (80 mg) were dissolved in 1 mL chloroform, respectively. NAS solution was then added into spermine solution gradually at room temperature under vigorous stirring. After overnight reacting, the mixture was filtered to remove by-products. The filtrate was then dried by rotary evaporation, followed by re-dispersing with ddH2O. After removal of insoluble substance, the solution was lyophilized. Finally, acryl-spermine was purified by process TLC. One of skill in the art that this is an exemplary method of manufacturing acryl-spermine and will understand that alternative methods could be used to reach the same result.

As illustrated in FIG. 2, the manufacture of a nanocapsules began with a positively charged, polymerizable monomer. For purposed of this example, the positively charged, polymerizable monomer is acryl-spermine which was prepared as described above. The first step of the process of manufacturing the polymer nanocapsules required electrostatic interactions enriched around the surface of the negatively charged siRNA. After the initial interactions, subsequent room-temperature polymerization in an aqueous solution took place with the pH-degradable crosslinkers and hydrophilic monomers. During the room temperature polymerization, each siRNA molecule was wrapped in a thin shell of polymer network. Such a crosslinked shell served to protect the cored siRNA from hydrolysis. Specific tuning of the ration of the acryl-spermine and the hydrophilic monomers allowed precise control of the surface charge and ensured the effective cellular transduction of the polymer nanocapsules. Moreover, 2 is stable in neutral pH but are rapidly degraded in acidic environment, such as late endosomes with pH~5.4. We believe that this unique responsive design will provide the polymer nanocapsules with outstanding stability in serum (pH~7.4), while enabling their escape from endosomes upon the degrading of the shell that releases the siRNA to the cytoplasma (Step IV). Furthermore, our synthetic approach allows for the immobilization of targeting components (e.g., antibody) to the polymer nanocapsules surface, allowing targeting delivery of siRNA.

Example 3. Ability of Nanocapsules to Protect and Deliver Encapsulated siRNA

In order to test the efficacy of the polymer nanocapsules described herein, a single siRNA nanocapsule platform that efficiently delivers siRNA was generated. Schematics of how the polymer nanocapsules are made are depicted in FIG. 1 and FIG. 2. These nanocapsules of this platform were designed to protect the encapsulated siRNA from nucleases and can effectively deliver siRNA into cells.

In order to test the ability of the polymer nanocapsules to protect the encapsulated siRNA and effectively deliver the siRNA into cells, the well known siRNA1005 was used in the preparation of the polymer nanocapsules. siRNA1005 is a short hairpin RNA (shRNA) that targets the HIV-1 co-receptor CCR5. The well-characterized potency of siRNA1005 made it an ideal candidate for demonstrating CCR5 knockdown by applying the single molecule nanocapsule delivery technology. Exemplary images of nanocapsules with siRNA1005 are presented in FIG. 4 and FIG. 5.

As proof of concept we showed that CCR5 RNA can be effectively knocked down by nanocapsules of siRNA1005. One unique advantage of this nanocapsule platform is the ability to modify the polymer nanocapsules by selecting monomers and crosslinkers which alter the chemical properties of size, charge, and reactivity of the particles. Non-limiting examples of monomers and crosslinkers can be found in Table 1 and Table 2.

The ability of the polymer nanocapsules to effectively protect encapsulated materials from degradation, was also demonstrated by encapsulating proteins. For example, EGFP, HRP, and caspase 3 were encapsulated and protected in the polymer nanocapsules. Furthermore, the polymer nanocapsules were also used to encapsulated quantum dots and siRNAs such as siEGFP, siLuciferase, and si1005 as described above.

Example 4. Delivery of siRNA Using DNA that Encodes shRNA

Delivery of siRNA was accomplished using DNA that encodes shRNA transcriptional units. For example, plasmid and viral vectors were used because they provide high levels and long term expression of the siRNA.

In this example, the polymer nanocapsule technology was further extended to nanocapsules of DNA encoding shRNA1005. As described in Example 3, shRNA1005 is an RNAi that targets and knocks down the expression of CCR5 RNA expression. This DNA nanocapsule technology is more challenging than the above described RNAi nanocapsule because DNA transcription units are much larger than siRNA.

The formulation of polymer nanocapsules platform for encapsulation of DNA cassettes was modified by tuning monomers and crosslinkers which alter the size, charge, and degradability of the particles. Non-limiting examples of monomers and crosslinkers are provided in Table 1 and Table 2.

Of particular interest, the polymer nanocapsules were engineered for delayed release using crosslinkers that degrade at different rates, enabling effective siRNA activity over several days or weeks. This is a big advantage over current small molecule drugs that are required daily administration Example 5. Synthesis and Delivery of DNA Nanocapsules As illustrated in FIG. 1, starting with the monomer A and B, crosslinker C, these molecules self-assembled along the surface of the DNA cassettes through electrostatic interaction and hydrogen bonding (Step 1). Then a thin network of polymer shell was formed around the DNA cassette by subsequent in situ polymerization (Step 2), which effectively confered new surface properties that protect the DNA. Crosslinker C was a non-degrable crosslinker. Acid-degradable crosslinkers D were stable in neutral pH but were rapidly degraded in acidic environment, such as late endosomes with pH around 5.4.

This unique responsive design provided the polymer nanocapsules with outstanding stability in the physiological pH of serum (pH~7.4). It also led to effective endosomal escape due to the "proton-sponge" effect resulting from the positive charges of monomers B and enabled controllable release of the DNA cassette into the cytoplasm upon the degradation progress of the shell. The DNA cassette then entered the nucleus and allowed the endogenous generation of siRNA (Step 4).

Example 6. DNA Nanocapsule Incorporating Short Linear DNA Cassettes

As proof of concept, we designed a model DNA nanocapsule incorporating a short linear DNA cassette with H1 expressed sh1005 shRNA and H1 expressed anti-EGFP shRNA as control. Delivery of a large DNA plasmid, consisting of shRNA transcriptional units and antibiotic resistance genes, was hindered by delivering barriers at the cell membrane and nucleopore. Accordingly a second DNA cassette was manufactured using a minimized linear DNA cassette of only 395 base pairs that was produced by PCR. The DNA cassette of only 395 base pairs, was able to transfer nucleopores more efficiently.

Gel electrophoresis image of these two DNA cassettes was shown in FIG. 3A. Interestingly, the TEM image of linear naked DNA cassette stained with tungsten agent appeared as a dark half circular arc with a diameter about 50 nm. In contrast, the DNA cassette nanocapsules had a round morphology with a much smaller size of approximately 30 nm. This is likely a result of DNA condensation through complexing with polymers.

Compared to previously reported nanoparticles that contain plasmid DNA (approximately 150-300 nm), the size of DNA cassette nanoparticles is remarkably ⅒ to ⅕ the size. This small size of the DNA cassette nanocapsules likely leads to a high diffusional rate and improve the delivery efficiency.

Example 7. DNA Cassette Nanocapsules are Efficiently Delivered to Cells

DNA cassette nanocapsules of this invention can be effectively delivered to cells. The optical and fluorescent images of HEK-293T cells after incubation with Alexa592-labeled DNA cassette nanocapsules for 4 hrs is shown in FIG. 4 and FIG. 5. The intense green fluorescence demonstrates delivery of the FITC-labeled siRNA nanocapsules (FIG. 4 and FIG. 5).

Flow cytometry of HEK-293 T cells transduced with Alexa592-labeled DNA cassette nanocapsules confirmed the results of the fluorescence imaging and demonstrated successful delivery of fluorescence-labeled siRNA nanocapsule (FIG. 5C).

RNAi activity of the DNA nanocapsule in 293T cells expressing a fusion of CCR5 and luciferase reporter gene sequence with CCR5-shRNA (sh1005) was also examined (FIG. 5D). The CCR5-shRNA DNA nanocapsules down-regulated about 80% of the bioluminescence intensity reflecting the knockout of the CCR5-luciferase fusion mRNA while cells treated with control DNA cassette nanocapsules did not exhibit significant decreases in the luciferase activity.

To investigate the sensitivity of DNA nanocapsules against Dnase I, DNA complexed with Lipofectamine® and DNA nanocapsules were incubated with Dnase I for 1 hour (FIG. 6A).

After acid treatment and DNA extraction, agarose gel electrophoresis showed such nanocapsules were able to proted and maintain the integrity of the encapsulated DNA. In contrast, non-encapsulated DNA in the native state and non-encapsulated DNA that was formulated with Lipofectamine® degraded. The DNA nanocapsules did not show obvious cytotoxicity at the concentration of DNA cassette below 0.4 pmol. At 0.4 pmol, the viability of cells treated with DNA nanocapsules was slightly reduced to about 85% (FIG. 7).

Example 8. siRNA Nanocapsules are Efficiently Delivered to Cells and Target Specific Sequences FIG. 4A shows a representative TEM image of the double-stranded siRNA nanocapsules which target CCR5 sequence 3'-gagcatgactgacatctac-5' with an average diameter of 25 nm. Interestingly, within each nanocapsule, a dark core with diameter around 5 nm was clearly observed, which is due to preferred complexation of siRNA with the tungsten-staining agent used for TEM observation. Since a double-stranded siRNA (21 base pairs) has an average molecular weight of 12 kDa and size of 3-5 nm, each of the polymer nanocapsules appears to only contain one siRNA molecule. FIG. 4B shows a fluorescent image of HEK-293 T cells after incubation with FITC-labeled siRNA for 4 hrs. The intense green fluorescence proves the effective delivery of the siRNA nanocapsules.

As proof of concept, CCR5-siRNA was used to target and down-regulate CCR5 expression. It has been well demonstrated that individuals born with naturally existing mutations in the CCR5 chemokine receptor are protected from HIV infection and disease progression. CCR5-siRNA holds great promise as a therapeutic drug to downregulate CCR5 expression and to develop HIV resistance in patients. To prove this concept, FIG. 4C shows flourescence images of HEK 293 cells transducted with siRNA nanocapsules targeted to CCR5 sequence (left panel of image in FIG. 4C) and EGFP sequence (right panel of image in FIG. 4C). Clearly, delivery of the CCR5-siRNA nanocapsules effectively down-regulates the CCR5-mCherry fusion protein expression. This demonstrates the effectiveness of siRNA nanocapsules delivery and function.

Luciferase-expressing CWR cells stably expressing luciferase were used to test the gene-silencing efficacy of single siRNA nanocapsules (FIG. 14A). Cells treated with luciferase siRNA nanocapsules showed a significant decrease in the luciferase activity especially at concentrations above 50 nM, while cells treated with control siRNA nanocapsules did not exhibit significant decrease in the luciferase activity. The siRNA nanocapsules did not show obvious cytotoxicity at the concentration of siRNA below 200 nM. At 300 nM, the viability of cells treated with siRNA nanocapsules was slightly reduced to about 75% (FIG. 14B).

Furthermore, without human serum, nanocapsules and Lipofectamine® (Invitrogen®) silenced expression of CCR5-mCherry expression to 8% and 15%, respectively. But in the presence of human serum, CCR5 siRNA nanocapsules still knocked down more than 85% of CCR5-mCherry expression while siRNA delivered through Lipofectamine® only made a number at 45%. Therefore, nanocapsules can provide extra protection and stabilization to siRNA inside against attacking of human serum nucleases compared with Lipofectamine®.

Example 9. DNA Cassette Nanocapsules Efficiently Knockdown Gene Expression in Cells The knockdown efficacy of DNA cassette nanocapsule was compared to standard Lipofectamine® siRNA transduction to HEK 293T cells expressing CCR5-luciferase fusion protein (FIG. 8).

After 48 hours, 0.1 pmol of sh1005 DNA cassette nanocapsule silenced the expression of CCR5-luciferase to 45%. In stark contrast, 100 pmol (1000× the amount) of siRNA-Lipofectamine® complex was required to knock down the level of CCR5-luciferase to 47%. On a molar basis, the sh1005 DNA cassette nanocapsule is over 1000-fold more effective at downregulating CCR5 than si1005 siRNA formulated with Lipofectamine® (FIG. 7 and FIG. 8). This result is likely due to de novo transcription of shRNA within transduced cells.

Example 10. Delayed Release and Degradable Nanocapsules

Because of the high potency of the DNA cassette nanocapsules, DNA cassette nanocapsules can be used in applications where sustained activity is beneficial. To accomplish this, DNA cassette nanocapsules were engineered for delayed release using crosslinkers that degrade at different rates.

The DNA nanocapsules prepared with 100% degradable crosslinkers (e.g., Glycerol 1,3-diglycerolate diacrylate, GDGDA) (5:0) was degraded completely after 10 hours. The DNA nanocapsules prepared with a mixture of one part degradable crosslinker to four parts non-degradable crosslinker (e.g., N,N'-methylene bisacrylamide, BIS) was completely degraded after 150 hours (FIG. 9). The slopes of the degradation profiles consistently increase with the percentage of degradable crosslinkers. This confirms that a higher percentage of the degradable crosslinkers leads to a higher degradation rate.

Using 100% of degradable crosslinker, the downregulation of CCR5 reached 70% at day 3 and 5 following transduction and decreased to 23% at day 9 (FIG. 10).

When the ratio of degradable crosslinker to non-degradable crosslinker is 3:2, the knockdown of CCR5 increased from 58% at day 3 to 70% at day 5 and then decreased to 42%.

The DNA nanocapsule with the ratio of degradable crosslinker to non-degradable crosslinker at 2:3, the silencing percentage of the CCR5 increased from 53% to 64% and further increased to 73%. By using 20% degradable crosslinker, the down regulation of CCR5 was as low as 20% at day 3 and reached 80% at day 9.

Example 11. Visualization Nanocapsules

IR spectra of the polymer nanocapsules were obtained on a PerkinElmer Paragon 1000 FT-IR spectrometer. UV-Visible spectra were acquired with a GeneSys 6 spectrometer (Thermo Scientific). Fluorescence spectra were obtained with a QuantaMaster Spectrofluorimeter (Photon Technology International). TEM images of nanocapsules were obtained on a Philips EM120 TEM at 100000× (see, e.g., FIG. 3, FIG. 4, and FIG. 5).

Before observation, siRNA nanocapsules were negatively stained using 1% pH 7.0 phosphotungstic acid (PTA) solution. Zeta potential and particle size distribution were measured with a Malvern particle sizer Nano-ZS. SEM images of nanocapsules were obtained with a JEOL JSM-6700F SEM. Dry samples on a silicon surface were sputter-coated with gold before measurement. Fluorescent images of cells were obtained with either Zeiss Axio Observer.Z1 fluorescence microscope or Leica TCS SP MP Inverted Confocal Microscope. Cellular fluorescent intensity distribution was determined with Becton Dickinson FACScan Analytic Flow Cytometer. A 488 nm argon laser was used as the excitation light.

Example 12. Synthesis of siRNA Nanocapsules

In situ polymerization and the process of manufacturing siRNA nanocapsules with different types and ratios of siRNA was optimized. Specifically, positively charged monomer, hydrophilic monomer and degradable cross-linkers were used to optimize the siRNA nanocapsules.

The effects of buffer salt, ion types, ionic strength and solvent composition on the morphology and yield of siRNA nanocapsules was assessed.

Varieties of targeting components were conjugated to the siRNA nanocapsules to achieve targeted delivery of the siRNA. For example, targeting conjugates used in these experiments included CD4, CD8, CD45, aHLA, and transferrin. These exemplary conjugates can be used alone or in combination to achieve specific targeting of the polymer nanocapsules.

FIG. 22 depicts the targeting delivery of siRNA to 293 cells expressing CD4 receptors. FIG. 22A shows the flow cytometry graph of 293 cells expressing CD4 receptors after incubation with FITC-labeled siRNA nanocapsules conjugated with anti-CD4 antibody for 4 hours. FIG. 22B shows the flow cytometry graph of regular 293 cells without CD4 receptors after incubation with FITC-labeled siRNA nanocapsules conjugated with anti-CD4 antibody for 4 hours.

Example 13. Characterization of the Nanocapsules

TEM and dynamic light scattering were used to determine the size and size distribution of single-siRNA nanocapsules. Furthermore, electrophoresis and electrophoretic light scattering was used to investigate the surface charge and the interaction between siRNA and nanocapsules. Specifically, size, surface charge, and encapsulation yield were investigated.

The stability of siRNA and single-siRNA nanocapsules in the presence of nuclease and serum was compared. Degradability and releasing profile of siRNA nanocapsules has been investigated in the buffer of pH 7.4 and 5.4. siRNA complexed with lipofectamine and siRNA nanocapsules was incubated with nuclease and human serum for 1 hour. After RNA extraction, agarose gel electrophoresis showed such nanocapsules could maintain the integrity of siRNA inside (FIG. 6B), while siRNA is degraded at the same time in the native state or when formulated with lipofectamine.

Example 14. Intracellular Delivery of the siRNA Nanocapsules

The siRNA delivery efficiency of the siRNA nanocapsules was tested in a broad variety of cells. Examples of these cells include HEK-293 T, Hela, CEM, PBMCs, and MSCs.

Fluorescence-labeled siRNA was used to investigate the endocytosis pathway using endocytosis inhibitors. The efficiency and toxicity of siRNA delivery by nanocapsules was compared with those by the commercial liposome agents. Different types of siRNA including, CCR5, EGFP, Gaussia luciferase was used to quantitatively assess specificity of gene silencing.

Example 15. In Vitro Cellular Internalization

Cellular internalization studies were performed via fluorescence microscopic technique and fluorescence-activated cell sorting (FACS). HeLa cells were cultured in Dulbecco's modified Eagle's medium (DMEM) supplemented with 10% bovine growth serum (BGS) and 1% penicillin/streptomycin. Cells (20000 cells/well, 24-well plate) were seeded the day before adding the siRNA nanocapsules.

siRNA nanocapsules with different concentrations were added into the cell medium. After incubation at 37° C. for 2 to 4 hrs, the cells were washed three times with PBS and either visualized with a fluorescent microscope or trypsinized, centrifuged, and re-suspended in PBS and analyzed via FACS.

Example 16. Cell Proliferation Assay

The toxicity of the polymer nanocapsules was assessed by the MTT assay using native proteins as control. HEK 293T cells (7000 cells/well) were seeded on a 96-well plate the day before exposure to the polymer nanocapsules. Nanocapsules with different concentrations were incubated with the cells for 2-4 hrs, removed from the mixture, and incubated with fresh media for 24 hrs. The MTT solution (20 µL) was added to each well and incubated for 3 h. The medium was then removed and 100 µL DMSO was added onto the cells. The plate was placed on a shaking table, 150 rpm for 5 min to thoroughly mix the solution, and then absorbance readings were measured at 560 nm. Untreated cells were used as the 100% cell proliferation control.

Example 17. Synthesis of Positively Charged Monomers for siRNA Nanocapsules

The preparation of N-(3-((4-aminobutyl)amino)propyl) acrylamide, N-(2-((2-aminoethyl)(methyl)amino)ethyl) acrylamide, N-(piperazin-1-ylmethyl) acrylamide, and N-(2-(bis(2-aminoethyl)amino)ethyl)acrylamide (i.e., positively charged monomers) was achieved by reacting amine-containing precursor (N-(3-aminopropyl) butane-1,4-diamine/N-methylpropane-1,3-diamine/piperazin-1-ylmethanamine/N,N'-bis(2-aminoethyl)ethane-1,2-diamine) with acrylic acid, hydroxysuccinimide ester (AHS). Briefly, amine-containing precursors and AHS were dissolved in chloroform at 0.5 mol/L, respectively. Then, acrylic acid, hydroxysuccinimide ester was added into each of the amine-containing precursors at the molar ratio of 1:1 gradually at room temperature under vigorous stirring. After overnight reaction, the mixture was filtered to remove by-products. The filtrate was then dried by rotary evaporation, followed by re-dispersing in water. After removal of insoluble substance, the solution was lyophilized. Finally, the product was purified by thin layer chromatography. The yield was from 37% to 63%. $^{1H}$NMR was performed to confirm the final products.

$^{1H}$ NMR for N-(3-((4-aminobutyl)amino)propyl)acrylamide produced the following peaks at 400 MHz, $D_2O$: 6.46 (m, 1H, $CH_2$=CHCO), 5.65 (m, 2H, $CH_2$=CHCO), 3.27 (m, 2H, CONH—$CH_2$), 2.78 (m, 10H, $CH_2$—NH—$CH_2$ and $CH_2$—$NH_2$), 1.75 (m, 4H, NH—$CH_2$—$CH_2$), 1.23 (m, 4H, NH—$CH_2$—$(CH_2)_2$—$CH_2$—NH)

$^{1H}$ NMR for N-(piperazin-1-ylmethyl) acrylamide produced the following peaks at 400 MHz, D$_2$O: 6.53 (m, 1H, CH$_2$═CHCO), 5.69 (m, 2H, CH$_2$═CHCO), 3.91 (m, 2H, CONH—CH$_2$—N), 2.28 (m, 4H, CH$_2$—NH—CH$_2$), 2.75 (m, 4H, CH$_2$—NH—CH$_2$).

$^{1H}$ NMR for N-(2-((2-aminoethyl)(methyl)amino)ethyl) acrylamide (400 MHz, D$_2$O): 6.39 (m, 1H, CH$_2$═CHCO), 5.58 (m, 2H, CH$_2$═CHCO), 3.18 (m, 2H, CONH—CH$_2$—N), 2.54 (m, 2H, CH$_2$—NH—CH$_3$), 3.22 (m, 3H, NH—CH$_3$)

$^{1H}$ NMR for N-(2-(bis(2-aminoethyl)amino)ethyl)acrylamide produced the following peaks at 400 MHz, D$_2$O: 6.41 (m, 1H, CH$_2$═CHCO), 5.62 (m, 2H, CH$_2$═CHCO), 3.14 (m, 2H, CONH—CH$_2$—N), 2.48 (m, 6H, N—(CH$_2$)$_3$), 2.65 (m, 4H, CH$_2$—NH$_2$).

Example 18. Synthesis of Positively Charged Monomers for siRNA Nanocapsules

The preparation of N-(3-((4-((3-aminopropyl)amino)butyl)amino)propyl)methacrylamide, N-(3-((4-aminobutyl)amino)propyl)methacrylamide, N-(2-((2-aminoethyl)(methyl)amino)ethyl)methacrylamide, N-(piperazin-1-ylmethyl) methacrylamide, and N-(2-(bis(2-aminoethyl)amino)ethyl)methacrylamide (i.e., positively charged monomers) was achieved by reacting (N,N'-(butane-1,4-diyl)bis(propane-1,3-diamine)/N-(3-aminopropyl) butane-1,4-diamine/N-methylpropane-1,3-diamine/piperazin-1-ylmethanamine/N,N-bis(2-aminoethyl)ethane-1,2-diamine)) with methacrylic acid, hydroxysuccinimide ester. Briefly, amine-containing precursors and methacrylic acid, hydroxysuccinimide ester were dissolved in 1 mL chloroform at 0.5 mol/L, respectively. The MAHS was then added into one of the amine-containing precursor at the molar ratio of 1:1 gradually at room temperature under vigorous stirring. After overnight reacting, the mixture was filtered to remove by-products. The filtrate was then dried by rotary evaporation, followed by re-dispersing with ddH2O. After removal of insoluble substance, the solution was lyophilized. Finally, the product was purified by thin layer chromatography. The yield was from 32% to 61%. $^{1H}$NMR was performed to confirm the final products.

$^{1H}$ NMR for N-(3-((4-((3-aminopropyl)amino)butyl)amino)propyl) methacrylamide produced the following peaks at 400 MHz, D$_2$O: 1.89 (m, 3H, CH$_2$═C(CH$_3$)CO), 5.72 (m, 2H, CH$_2$═C(CH$_3$)CO), 3.27 (m, 2H, CONH—CH$_2$), 2.78 (m, 10H, CH$_2$—NH—CH$_2$ and CH$_2$—NH$_2$), 1.75 (m, 4H, NH—CH$_2$—CH$_2$), 1.23 (m, 4H, NH—CH$_2$—(CH$_2$)$_2$—CH$_2$—NH).

$^{1H}$ NMR for N-(3-((4-aminobutyl)amino)propyl)methacrylamide produced the following peaks at 400 MHz, D$_2$O: 1.92 (m, 3H, CH$_2$═C(CH$_3$)CO), 5.75 (m, 2H, CH$_2$═C(CH$_3$)CO), 3.27 (m, 2H, CONH—CH$_2$), 2.78 (m, 10H, CH$_2$—NH—CH$_2$ and CH$_2$—NH$_2$), 1.75 (m, 4H, NH—CH$_2$—CH$_2$), 1.23 (m, 4H, NH—CH$_2$—(CH$_2$)$_2$—CH$_2$—NH).

$^{1H}$ NMR for N-(piperazin-1-ylmethyl) methacrylamide produced the following peaks at 400 MHz, D$_2$O: 1.90 (m, 3H, CH$_2$═C(CH$_3$)CO), 5.72 (m, 2H, CH$_2$═C(CH$_3$)CO), 3.91 (m, 2H, CONH—CH$_2$—N), 2.28 (m, 4H, CH$_2$—NH—CH$_2$), 2.75 (m, 4H, CH$_2$—NH—CH$_2$).

$^{1H}$ NMR for N-(2-((2-aminoethyl)(methyl)amino)ethyl) methacrylamide produced the following peaks at 400 MHz, D$_2$O: 1.94 (m, 3H, CH$_2$═C(CH$_3$)CO), 5.62 (m, 2H, CH$_2$═C(CH$_3$)CO), 3.18 (m, 2H, CONH—CH$_2$—N), 2.54 (m, 2H, CH$_2$—NH—CH$_3$), 3.22 (m, 3H, NH—CH$_3$).

$^{1H}$ NMR for N-(2-(bis(2-aminoethyl)amino)ethyl)methacrylamide produced the following peaks at 400 MHz, D$_2$O: 1.93 (m, 3H, CH$_2$═C(CH$_3$)CO), 5.67 (m, 2H, CH$_2$═C(CH$_3$)CO), 3.14 (m, 2H, CONH—CH$_2$—N), 2.48 (m, 6H, N—(CH$_2$)$_3$), 2.65 (m, 4H, CH$_2$—NH2).

Example 19. Synthesis of siRNA Nanocapsules siRNA was dissolved in 20 uL RNase-free water at 20 uM. Then a specific amount of positively charged monomers, tris-acrylamide and glycerol dimethacrylate (molar ratio=5:5:1) dissolved in 0.5 mL deoxygenated and deionized water was added to the microcentrifugetube. Radical polymerization from the surface of the acryloylated protein was initiated by adding 0.02 mg of ammonium persulfate dissolved in 2 µL of deoxygenated and deionized water and 0.4 µL of N,N,N',N'-tetramethylethylenediamine. The reaction was allowed to proceed for 60 min in a nitrogen atmosphere.

Example 20. Effect of Positively Charged Monomers on siRNA Knockdown of Gene Expression To test the effect of the positively charged monomers provided in Table 1, siRNA nanocapsules were prepared with siRNA against luciferase gene expression with each of the 14 individual positively charged monomers in Table 1. These knockdown experiments were conducted in luciferase expressing CWR cells.

To prepare the polymer nanocapsules, siRNA was dissolved in 20 uL Rnase-free water at 20 uM. Then a specific amount of a positively charged monomer selected from Table 1, tris-acrylamide and glycerol dimethacrylate (total number of protonable amines of positively charged monomer:tris-acrylamide:glycerol demethacrylate=15:5:1) were dissolved in 0.5 mL deoxygenated and deionized water was added to the microcentrifugetube. Radical polymerization from the surface of the acryloylated protein was initiated by adding 0.02 mg of ammonium persulfate dissolved in 2 µL of deoxygenated and deionized water and 0.4 µL of N,N,N',N'-tetramethylethylenediamine. The reaction was allowed to proceed for 60 min in a nitrogen atmosphere.

CWR cells were treated with siRNA nanocapsules at 50 nM for 4 h at 37° C. in serum-free medium. Then mediums were changed to DMEM with 10% Bovine Fetal Serum. After 48 h, the luciferase activity was determined using a 96-wells plate reader (FIG. 11).

Example 21. Effect of Different Crosslinkers on siRNA Knockdown of Gene Expression To test the effect of the crosslinkers provided in Table 2 on gene knockdown, siRNA nanocapsules were prepared with siRNA against luciferase gene expression with 1,3-glycerol dimethacrylate, Glycerol 1,3-diglycerolate diacrylate, N,N'-bis(acryloyl)cystamine, bis[2-(methacryloyloxy)ethyl]phosphate, or N,N'-Methylenebisacrylamide (Table 2). These knockdown experiments were conducted in luciferase expressing CWR cells.

To prepare the polymer nanocapsules, siRNA was dissolved in 20 uL Rnase-free water at 20 uM. Then a specific amount of acryl-spermine, tris-acrylamide and a crosslinker from Table 2 (total number of protonable amines of positively charged monomer:tris-acrylamide:crosslinker=15:5:1) were dissolved in 0.5 mL deoxygenated and deionized water was added to the microcentrifugetube. Radical polymerization from the surface of the acryloylated protein was initiated by adding 0.02 mg of ammonium persulfate dissolved in 2 μL of deoxygenated and deionized water and 0.4 μL of N,N,N',N'-tetramethylethylenediamine. The reaction was allowed to proceed for 60 min in a nitrogen atmosphere.

CWR cells were treated with siRNA nanocapsules at 50 nM for 4 h at 37° C. in serum-free medium. Then mediums were changed to DMEM with 10% Bovine Fetal Serum. After 48 h, the luciferase activity was determined using a 96-wells plate reader (FIG. 12).

Example 21. Effect of Different Neutral Monomers on siRNA Nanocapsule Size

To test the effect of the neutral monomers provided in Table 3 on nanocapsules size, siRNA nanocapsules were prepared with 1N-(1,3-dihydroxy-2-(hydroxymethyl) propan-2-yl) acrylamide, acrylamide, N-(hydroxymethyl)acrylamide, 2-hydroxyethyl acrylate, or 2-hydroxyethyl methacrylate (Table 3).

To prepare the polymer nanocapsules, siRNA was dissolved in 20 uL Rnase-free water at 20 uM. Then a specific amount of acryl-spermine, a neutral monomer selected from Table 3, and glycerol dimethacrylate (total number of protonable amines of acryl-spermine:neutral co-monomer:glycerol demthacrylate=15:5:1) were dissolved in 0.5 mL deoxygenated and deionized water was added to the microcentrifugetube. Radical polymerization from the surface of the acryloylated protein was initiated by adding 0.02 mg of ammonium persulfate dissolved in 2 μL of deoxygenated and deionized water and 0.4 μL of N,N,N',N'-tetramethylethylenediamine. Once the siRNA nanocapsules were formed, the size of the polymer nanocapsules were measured (FIG. 13).

The invention claimed is:

1. A polymer nanocapsule comprising a polymer shell and a nucleic acid selected from the group consisting of: an siRNA, an shRNA expression DNA cassette, and a dsRNA, wherein the polymer shell comprises
   a. one or more positively charged monomers selected from the group consisting of: N-(3-((4-((3-aminopropyl)amino)butyl)amino)propyl)acrylamide, N-(3-((4-((3-aminopropyl)amino)butyl)amino)propyl)methacrylamide, N-(3-((4-aminobutyl)amino)propyl) acrylamide, N-(3-((4-aminobutyl)amino)propyl) methacrylamide, N-(2-((2-aminoethyl)(methyl)amino) ethyl)acrylamide, N-(2-((2-aminoethyl)(methyl) amino)ethyl) methacrylamide, N-(piperazin-1-ylmethyl)acrylamide, N-(piperazin-1-ylmethyl) methacrylamide, N-(2-(bis(2-aminoethyl)amino)ethyl) acrylamide, N-(2-(bis(2-minoethyl)amino)ethyl) methacryl amide, (3-acrylamidopropyl) trimethylammonium hydrochloride, and 2-aminoethyl methacrylate;
   b. one or more crosslinkers selected from the group consisting of: 1,3-glycerol dimethacrylate, glycerol 1,3-diglycerolate diacrylate, N,N'-bis(acryloyl)cystamine, bis[2-(methacryloyloxy)ethyl]phosphate, N,N'-Methylenebisacrylamide, bisacryloylated polypeptide, and
   c. one or more neutral monomers selected from the group consisting of: N-(1,3-dihydroxy-2-(hydroxymethyl) propan-2-yl)acrylamide, acrylamide, N-(hydroxymethyl)acrylamide, 2-hydroxyethyl acrylate, 2-hydroxyethyl methacrylate,
   and wherein the polymer shell encapsulates the nucleic acid.

2. The polymer nanocapsule of claim 1, wherein one or more crosslinkers comprise:
   a) a degradable crosslinker selected from the group consisting of: 1,3-glycerol dimethacrylate, glycerol 1,3-diglycerolate diacrylate, N,N'-bis(acryloyl)cystamine, bis[2-(methacryloyloxy)ethyl]phosphate and bisacryloylated polypeptide; and
   b) a non-degradable crosslinker, wherein said non-degradable cross linker is N,N'-methylenebisacrylamide, wherein the ratio of degradable crosslinker to non-degradable crosslinker is selected from the ratios comprising 1:0, 3:2, 2:3, or 1:4.

3. The polymer nanocapsule of claim 1, wherein all of the crosslinkers are selected from the group consisting of: 1,3-glycerol dimethacrylate, glycerol 1,3-diglycerolate diacrylate, N,N'-bis(acryloyl)cystamine, bis[2-(methacryloyloxy)ethyl]phosphate and bisacryloylated polypeptide.

4. The polymer nanocapsule of claim 3, wherein all the crosslinkers are glycerol 1,3-diglycerolate diacrylate.

5. The polymer nanocapsule of claim 1, wherein the polymer nanocapsules are approximately 20 nm to 250 nm in diameter.

6. The polymer nanocapsule of claim 1, wherein the polymer nanocapsule is conjugated to a targeting agent.

7. The polymer nanocapsule of claim 6, wherein the targeting agent is an anti-CD4 targeting agent.

8. The polymer nanocapsule of claim 6, wherein the targeting agent delivers the polymer nanocapsule to a specific cell type, wherein the cell type is selected from the group comprising immune cells, blood cells, cardiac cells, lung cells, optic cells, liver cells, kidney cells, brain cells, cells of the central nervous system, cells of the peripheral nervous system, cancer cells, cells infected with viruses, stem cells, skin cells, intestinal cells, and/or auditory cells.

9. The polymer nanocapsule of claim 8, wherein the cancer cells are cells selected from the group comprising lymphoma cells, solid tumor cells, leukemia cells, bladder cancer cells, breast cancer cells, colon cancer cells, rectal cancer cells, endometrial cancer cells, kidney cancer cells, lung cancer cells, melanoma cells, pancreatic cancer cells, prostate cancer cells, and thyroid cancer cells.

10. A pharmaceutical composition comprising one or more polymer nanocapsule of claim 1 and a pharmaceutically acceptable carrier.

11. A method of treating a disease characterized by over expression of a gene with a pharmaceutical composition of claim 10, wherein the siRNA or shRNA knocks down or decreases expression of an over expressed gene, thereby treating the disease.

12. The polymer nanocapsule of claim 1, wherein the polymer shell encapsulates a single nucleic acid molecule.

13. The polymer nanocapsule of claim 1, wherein the polymer nanocapsule comprises an siRNA.

14. The polymer nanocapsule of claim 1, wherein the polymer nanocapsule comprises an shRNA DNA cassette.

15. The polymer nanocapsule of claim 1, wherein the polymer nanocapsule comprises a dsRNA.

16. The polymer nanocapsule of claim 1, wherein the one or more positively charged monomer is N-(3-((4-((3-aminopropyl)amino)butyl)amino)propyl)acrylamide, the one or more crosslinkers is 1,3-glycerol dimethacrylate, and the one or more neutral monomers is N-(1,3-dihydroxy-2-(hydroxymethyl)propan-2-yl)acrylamide.

17. A polymer nanocapsule comprising a polymer shell and an siRNA molecule; wherein the polymer shell comprises N-(3-((4-((3-aminopropyl)amino)butyl)amino)propyl)acrylamide; 1,3-glycerol dimethacrylate; and N-(1,3-dihydroxy-2-(hydroxymethyl)propan-2-yl)acrylamide.

18. A polymer nanocapsule comprising a polymer shell and an shRNA, wherein the polymer shell comprises N-(3-((4-((3-aminopropyl)amino)butyl)amino)propyl)acrylamide; glycerol 1,3-diglycerolate diacrylate; and acrylamide.

* * * * *